United States Patent
Yano et al.

(10) Patent No.: US 10,251,378 B2
(45) Date of Patent: Apr. 9, 2019

(54) TRANSGENIC MOUSE EXPRESSING KIDNEY-SPECIFIC HUMAN TGF-BETA1, AND BIOMARKER FOR TISSUE FIBROSIS MOUSE MODEL

(71) Applicant: MIE UNIVERSITY, Tsu-shi (JP)

(72) Inventors: Yutaka Yano, Tsu (JP); Esteban C. Gabazza, Tsu (JP); Corina Gabazza, Tsu (JP)

(73) Assignee: MIE UNIVERSITY, Tsu-Shi (JP)

( * ) Notice: Subject to any disclaimer, the term of this patent is extended or adjusted under 35 U.S.C. 154(b) by 0 days.

(21) Appl. No.: 15/321,864

(22) PCT Filed: Jun. 24, 2015

(86) PCT No.: PCT/JP2015/068238
§ 371 (c)(1),
(2) Date: Dec. 23, 2016

(87) PCT Pub. No.: WO2015/199144
PCT Pub. Date: Dec. 30, 2015

(65) Prior Publication Data
US 2017/0135328 A1 May 18, 2017

(30) Foreign Application Priority Data

Jun. 25, 2014 (JP) ................................. 2014-130304

(51) Int. Cl.
| | | |
|---|---|---|
| *A01K 67/027* | (2006.01) | |
| *G01N 33/00* | (2006.01) | |
| *C12N 15/00* | (2006.01) | |
| *C12N 15/09* | (2006.01) | |
| *G01N 33/53* | (2006.01) | |
| *C07K 14/495* | (2006.01) | |
| *G01N 33/68* | (2006.01) | |

(52) U.S. Cl.
CPC ........ *A01K 67/0278* (2013.01); *C07K 14/495* (2013.01); *C12N 15/09* (2013.01); *G01N 33/53* (2013.01); *G01N 33/6863* (2013.01); *A01K 2207/15* (2013.01); *A01K 2217/072* (2013.01); *A01K 2227/105* (2013.01); *A01K 2267/035* (2013.01); *A01K 2267/0368* (2013.01); *C12N 2830/008* (2013.01)

(58) Field of Classification Search
USPC .............................................. 800/18, 21, 3
See application file for complete search history.

(56) References Cited

U.S. PATENT DOCUMENTS

2016/0374319 A1 12/2016 Gabazza et al.

FOREIGN PATENT DOCUMENTS

| JP | 2006006103 A | 1/2006 |
|---|---|---|
| JP | 2013094071 A | 5/2013 |
| WO | 2015087916 A1 | 6/2015 |

OTHER PUBLICATIONS

Macary (Virchows Arch., 2010, vol. 456, p. 325-337).*
Chihiro Akazawa et al., "Establishing Sox10-VENUS transgenic mice utilizing BAC recombination in E. coli for analyses of neural crestopathy", Juntendo Medical Journal, 2009, vol. 55, pp. 34 to 39, and English summary attached at the end.
D.Drabek, et al., "The expression of bacterial nitroreductase in transgenic mice results in specific cell killing by the prodrug CB1954", Gene Therapy (1997), vol. 4, pp. 93-100.
English translation of International Preliminary Report on Patentability dated Nov. 25, 2016 for parent application No. PCT/JP2015/068238.
English translation of International Search Report dated Sep. 15, 2015 for parent application No. PCT/JP2015/068238.
Gong, S., et al., "Highly Efficient Modification of Bacterial Artificial Chromosomes (BACs) Using Novel Shuttle Vectors Containing the R6Kγ Origin of Replication", Genome Research 2002,vol. 12, pp. 1992-1998.
Guillaume Macary et al., "Transgenic mice expressing nitroreductase gene under the control of the podocin promoter: a new murine model of inductible glomerular injury", Virchows Archiv 2010, vol. 456, No. 3, pp. 325-337.
Heather E. Daly, et al., "Bleomycin Induces Strain-Dependent Alterations in the Pattern of Epithelial Cell-Specific Marker Expression in Mouse Lung"; Toxicology and Applied Pharmacology, vol. 142, pp. 303-310 (1997).
Tobias B. Huber, et al., "Interaction with Podocin Facilitates Nephrin Signaling", J. Biol. Chem., 2001, vol. 276, No. 45, pp. 41543-41546.
Jeffrey B. Kopp, et al., "Transgenic Mice with Increased Plasma Levels of TGF-β1 Develop Progressive Renal Disease", Laboratory Investigation, 1996, vol. 74, pp. 991-1003.
Keisuke Sugimoto, "The pathogenesis of interstitial pneumonia and the role of cytokines", Journal of Okayama Medical Association 1994, vol. 106, pp. 641 to 654 and English summary attached at the end.

(Continued)

*Primary Examiner* — Michael C Wilson
(74) *Attorney, Agent, or Firm* — J-Tek Law PLLC; Jeffrey D. Tekanic; Scott T. Wakeman

(57) ABSTRACT

A transgenic mouse has a genome that includes the entire gene region of human transforming growth factor beta-1 (human TGFβ1) located downstream of a mouse Podocin promoter such that expression of the human TGFβ1 is controlled by the mouse Podocin promoter. The human TGFβ1 contains 7 exons and 6 introns, the human TGFβ1 is expressed in a kidney of the mouse as non-active TGFβ1 and becomes active TGFβ1 extracellularly, and the transgenic mouse spontaneously develops renal fibrosis.

7 Claims, 19 Drawing Sheets
Specification includes a Sequence Listing.

(56) References Cited

OTHER PUBLICATIONS

Kuniya Abe, et al., "Establishment of an Efficient BAC Transgenesis Protocol and its Application to Functional Characterization of the Mouse Brachyury Locus", Exp Anim. 53(4), pp. 311-320 (2004).

Mitsuko Hara et al., "TGF-β in tissue fibrosis", Journal of Clinical and Experimental Medicine, 2010, vol. 234, No. 10, pp. 977-982.

Shu-Fen Liu et al, "Dioscorea alata Attenuates Renal Interstitial Cellular Fibrosis by Regulating Smad- and Epithelial-Mesenchymal Transition Signaling Pathways", PLOS ONE, 2012, vol. 7, Issue. 11, pp. 47482.

Tsutomu Inoue, "Hepatocyte Growth Factor (HGF) Prevent Progression of Renal Interstitial Fibrosis via Its Counteraction Against Transforming Growth Factor-beta (TGF-β) in 5/6 Nephrectomized Mice"; Journal of Saitama Medical University, 2002, vol. 29(1), pp. 13-26.

Wawaimuli Arozal, et al., "Effects of Angiotensin Receptor Blocker on Oxidative Stress and Cardio-Renal Function in Streptozotocin-Induced Diabetic Rats", Biol. Pharm. Bull. 32(8), pp. 1411-1416 (2009).

Yang, X., et al., "Homologous recombination based modification in *Esherichia coli* and germline transmission in transgenic mice of a bacterial artificial chromsome", Nature Biotechnology, 1997, vol. 15, pp. 859-865.

Youming Zhang, et al., "A new logic for DNA engineering using recombination in *Escherichia coli*"; Nature America Inc., vol. 20, Oct. 1998, pp. 123-128.

Written Opinion dated Sep. 15, 2015 in parent application No. PCT/JP2015/068238 and machine translation of substantive portions thereof.

\* cited by examiner (A) Wild type mouse/Saline (B) Wild type mouse/STZ (C) TGFβ1 TG mouse/STZ

TRANSGENIC MOUSE EXPRESSING KIDNEY-SPECIFIC HUMAN TGF-BETA1, AND BIOMARKER FOR TISSUE FIBROSIS MOUSE MODEL

CROSS-REFERENCE

This application is the US national stage of International Patent Application No. PCT/JP2015/068238 filed on Jun. 24, 2015, which claims priority to Japanese Patent Application No. 2014-130304 filed on Jun. 25, 2014.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
|---|---|---|
| MIE005_seq_list.txt | Dec. 23, 2016 | 3 |

TECHNICAL FIELD

The present invention relates to the transgenic (TG) mouse which expresses human TGFβ1 (human transforming growth factor β1; transformation (transforming) growth factor beta 1; hereinafter, "human TGFβ1" or "hTGFβ1") specifically in the kidney, and a biomarker for tissue fibrosis in mouse model.

BACKGROUND ART

Number of patients to develop hemodialysis have been increasing with the deterioration of kidney disease due to chronic diseases such as diabetes, collagen diseases and hypertension. More than about 10,000 patients per year have started a new dialysis. Since the prognosis of hemodialysis patients who have shifted from chronic disease to renal failure is significantly worse than that of other diseases, measures to improve prognosis have been urgently needed. In the early stage of the disease, the inflammatory response plays an important role in the pathogenesis of kidney damage. As the condition progresses, fibrosis occurs by abnormal epithelial and mesenchymal tissue reactions. Many factors including TGFβ1, connective tissue growth factor (CTGF), platelet-derived growth factor (PDGF), inflammatory cytokine, chemokine (C—C motif) ligand 2/monocyte chemotactic protein 1 (CCL 2), oxidizing agents and coagulation factors are considered as causes of tissue fibrosis.

TGFβ1 is a major cytokine in the pathogenesis of remodeling, including fibrosis and tissue repair in many organs, including the kidney. Many kinds of cells including macrophages, T cells, eosinophils, neutrophilsng and basophils produce TGFβ1. TGFβ1 is stored in a non-active form that is bound to a related protein (latency-associated protein (LAP)) in a cell. When the non-active TGFβ1 is separated from LAP by cathepsin, plasmin, calpain, thrombospondin, integrin-αvβ6 or metalloproteinase, which increase commonly in the process of fibrosis, activated TGFβ1 is released. According to experiments using genetically modified animals, kidney fibrosis associated with mononuclear cell infiltration is induced, when the active TGFβ1 concentration in the blood rises. TGFβ1 plays an important role in the kidney fibrosis. Meanwhile, active and latent TGFβ1 are observed at high concentrations in the blood, urine and kidney tissues of patients with severe renal fibrosis.

For research on human organ fibrosis and development of drugs related to organ fibrosis, model animals (for example, mouse etc.) expressing human TGFβ1 in a specific organ has been required. The present inventors have been studying human TGFβ1 for many years and succeeded in developing transgenic (TG) mouse expressing human TGFβ1 specifically in lung (Patent Document 1).

However, reports of TG mice expressing human TGFβ1 specifically in the kidney have been not observed. Therefore, there remains a situation in which research on kidney fibrosis has to be conducted using TG mouse expressing human TGFβ1 in other organs including kidney tissue (Non-Patent Document 1).

On the other hand, although a biomarker for a tissue fibrosis mouse model is known (Non-Patent Document 2), the biomarker only indicates the degree of inflammation associated with the process of fibrosis, and is not specific for tissue fibrosis.

PRIOR ART DOCUMENTS

Patent Document

Patent Document 1: JP2013-094071 A1

Non-Patent Documents

Non-Patent Document 1: Kopp J B, Factor V M, Mozes M, Nagy P, Sanderson N, Boettinger E P, Klotman P E, Thorgeirsson S S: Transgenic mice with increased plasma concentrations of TGF-β1 develop progressive renal disease. Lab Invest 1996; 74: 991-1003.

Non-Patent Document 2: Bleomycin induces strain-dependent alterations in the pattern of epithelial cell-specific marker expression in mouse lung. Toxicol Appl Pharmacol. 1997 February; 142(2):303-10.

Non-Patent Document 3: Zhang Y et al, A new logic for DNA engineering using recombination in E. Coli., Nature 20(1998) 123-128

Non-Patent Document 4: Exp Anim. 2004 53(4):311-20. Establishment of an efficient BAC transgenesis protocol and its application to functional characterization of the mouse Brachyury locus. Abe K, Hazama M, Katoh H, Yamamura K, Suzuki M.

SUMMARY OF THE INVENTION

A mouse that expresses TGFβ1 specifically in the kidney has been desired as a model mouse of kidney fibrosis. To date, such TG mouse has not been obtained.

Specific biomarkers of tissue fibrosis to evaluate the pathology of model mouse have not been known.

The present invention was made in view of the circumstances described above, and its objective is to provide TG mouse which expresses TGFβ1 specifically in the kidney and naturally develops renal fibrosis. Also, another objective is to provide biomarkers to evaluate the pathology of tissue fibrosis of a model mouse.

To accomplish the above-mentioned objectives, the non-human transgenic mammal of the present invention is characterized in that it comprises a non-human mammal Podocin promoter and the entire gene region of human transforming growth factor beta 1 (human TGFβ1) located downstream of the promoter and whose expression is controlled thereby. At this time, the transgenic non-human mammal is preferably selected from the group consisting of a mouse, a rat, a pig, a sheep, a horse and a cow, and is more preferably a mouse.

It is preferable that the human TGFβ1 is expressed in a kidney as non-active TGFβ1 and becomes active TGFβ1 extracellularly.

It is preferable that the entire gene region of the human TGFβ1 contains 7 exons and 6 introns.

The coding region of the mouse Podocin gene encodes a genomic sequence spanning 17 kb containing 8 exons and 7 introns. The coding region of the human TGFβ1 gene encodes a genomic sequence spanning 23 kb containing 7 exons and 6 introns. In the present invention, the mouse Podocin promoter is used, and the coding region of the whole human TGFβ1 gene is incorporated in place of the coding region of the Podocin gene. TGFβ1 is stocked in a cell as a non-active form that is associated with the relevant protein (LAP). Non-active TGFβ1 is cleaved from LAP outside the cell membrane by various factors (cathepsin, plasmin, calpain, thrombospazin, integrin-αvβ6, metalloproteinase, etc.) to become active TGFβ1. When trying to produce a transgenic mouse using cDNA prepared from mRNA as TGFβ1 instead of the entire gene region containing introns, active TGFβ1 is expressed in a large amount without going through non-active TGFβ1; therefore a transgenic mice expressing kidney-specific TGFβ1 could not be produced. In contrast, in the present invention, since the entire gene region including introns is used, the expression form is close to that of native TGFβ1. Therefore, the transgenic mouse is more useful for analyzing pathological conditions.

It is preferable that the non-human mammal is a mouse, and the transgenic mouse starts to develop renal fibrosis spontaneously from the age of 15 weeks.

It is preferable that the transgenic mouse line is C57BL/6J.

A method for producing the said transgenic mouse is characterized in that it comprises (1) a recombination step for preparing a gene for selection in which a selection cassette is incorporated in the intron of the human TGFβ1 gene in Bacterial Artificial Chromosome (BAC) containing the human TGFβ1 gene, (2) a creating and modifying step to obtain a modified human TGFβ1 gene fragment in which a homologous sequence to the sequence downstream of the mouse Podocin promoter is introduced to the 5'-side and 3'-side of the human TGFβ1 gene obtained in the recombination step for preparing a gene for selection, (3) a step for preparing a Podocin-human TGFβ1 gene fragment for selection in which, in the BAC containing the whole mouse Podocin coding sequence having the flanking sequence on the 5'-side and 3'-side, the modified human TGFβ1 gene fragment is transferred to the downstream side of the mouse Podocin promoter region, (4) a step for preparing a Podocin-TGFβ1 BAC transgenic construct in which the human TGFβ1 gene fragment for selection is removed, and (5) a step for obtaining a transgenic mouse in which the Podocin-TGFβ1 gene is purified from the Podocin-TGFβ1 BAC transgenic construct and is microinjected into a mouse embryo.

In the invention, it is preferable that the gene for selection is a streptomycin sensitive wild type ribosomal S12 protein gene (rpsl).

In the invention, a flanking sequence on the 5'-side and 3'-side to the whole mouse Podocin coding sequence means a sequence present on the 5'-side and 3'-side of the whole mouse Podocin coding sequence (gene), which can affect the expression of Podocin.

A method for evaluating the pathology of a human TGFβ1-expressing transgenic mouse according to the present invention is characterized in that it comprises (1) a step for obtaining a cut-off value, at which the transgenic mouse develops fibrosis, from the graph showing the correlation between the human TGFβ1 concentration in a bodily fluid and the CT fibrosis score, (2) a step for measuring the concentration of human TGFβ1 in the bodily fluid after collecting the bodily fluid from the transgenic mouse, and (3) comparing the cut-off value and the measured TGFβ1 concentration in the bodily fluid of the transgenic mice, and determining that the transgenic mouse has developed fibrosis when the concentration of human TGFβ1 in the bodily fluid is not less than the cut-off value.

A kit for carrying out the method for evaluating the pathological condition above is characterized in that it comprises an instrument for collecting a bodily fluid from the transgenic mouse, a tube to separate a component of the including human TGFβ1 from the collected bodily fluid and an ELISA for measuring the concentration of human TGFβ1. The cut-off value, which is the concentration of human TGFβ1 in a given bodily fluid, may be the lowest concentration at which fibrosis develops, or may be a concentration value that adds about 10% to the lowest value and expects a certain margin. It is also possible to set certain classifications and set multiple cut levels to estimate symptoms.

Further, a kit for diagnosing human fibrosis is characterized in that it comprises an instrument for collecting a bodily fluid from a subject, a tube for separating the component containing human TGFβ1 from the collected bodily fluid, an ELISA for measuring human TGFβ1.

In the present invention, a bodily fluid means blood, urine, saliva, tears, sweat, runny nose, sweat, secretions such as gastric juice, stored liquids such as thoracic ascites and the like (the same applies hereinafter).

In the present invention, an instrument means a syringe when using blood as the bodily fluid, a ureter or an urine collection tray when using urine, a cup with an appropriate size or a saliva collection tube when using saliva, a small spoon like a spatula or an eyedropper when using tears/runny/sweat, and a stomach tube when using gastric juice, a fixed tube or a syringe when using thoracic ascites.

In the present invention, a component containing human TGFβ1 refers mainly to extracellular liquid components. For example, in the case of blood, it means serum or plasma. In the case of other bodily fluids, the liquid portion is used as a liquid component for measurement or after solid-liquid separation by appropriate centrifugation or the like.

Filtration membranes with endothelial cells, basement membrane and podocytes are formed in the glomeruli of the kidney. In the filtration membranes, podocytes are lined along the opposite side of the glomerular basement membrane and exist in the back of the Bowman's capsule. Podocytes form a network with many pseudopods tightly intertwined to suppress the protein leakage from the glomeruli. Podocin is a protein specifically expressed in the space between the protrusions of adjacent podocytes. In the present invention, the Podocin promoter is used as a promoter for expressing human TGFβ1 specifically in the kidney. In addition to Podocin, nephrin, Glucocorticoid Induced Transcript-1 (GLCCT1) and the like are known as proteins expressed specifically in the kidney. According to the technical idea of the present invention, in addition to the Podocin promoter, other promoters of proteins specifically expressed in the kidney can be used.

According to the present invention, a TG mouse that expresses kidney-specific human TGFβ1 spontaneously develops renal fibrosis. By using the TG mouse, research on kidney-related diseases (including glomerular sclerosis, renal failure, diabetic nephropathy, hypertension-related renal disorders, kidney cancer and peritoneal fibrosis) can be dramatically advanced.

Further, according to the present invention, the pathology of transgenic mice expressing human TGFβ1 can be easily evaluated without CT examination.

[32 P] labeled Podocin-human TGFβ RecBAC by random prime method was hybridized by incubating with the Southern blot transferred fragments of genomic DNA from candidates of transgenic mouse founder individuals. Nylon membrane was washed to remove nonspecifically bound radioactive probes and specifically bound fragments were detected by autoradiography. The markers in the figure are M1: NEB and 1 KB ladder.

Figure 6:
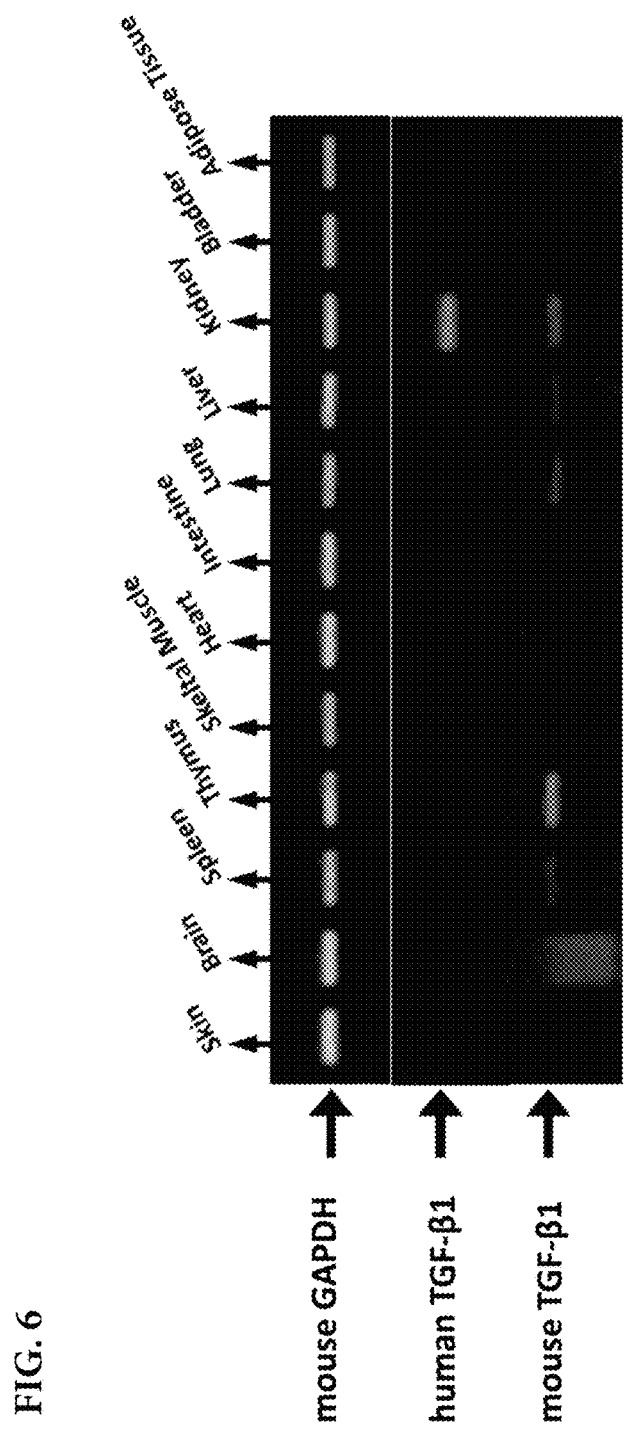

FIG. 6 is a photograph showing the results of reverse transcriptase polymerase chain reaction (RT-PCR) of mouse and human TGFβ1 in mouse Podocin-human TGFβ1 RecBAC-TG mouse. Expression of mouse TGFβ1 was found in almost all organs. On the other hand, expression of human TGFβ1 was found only in the kidney.

Figure 7:
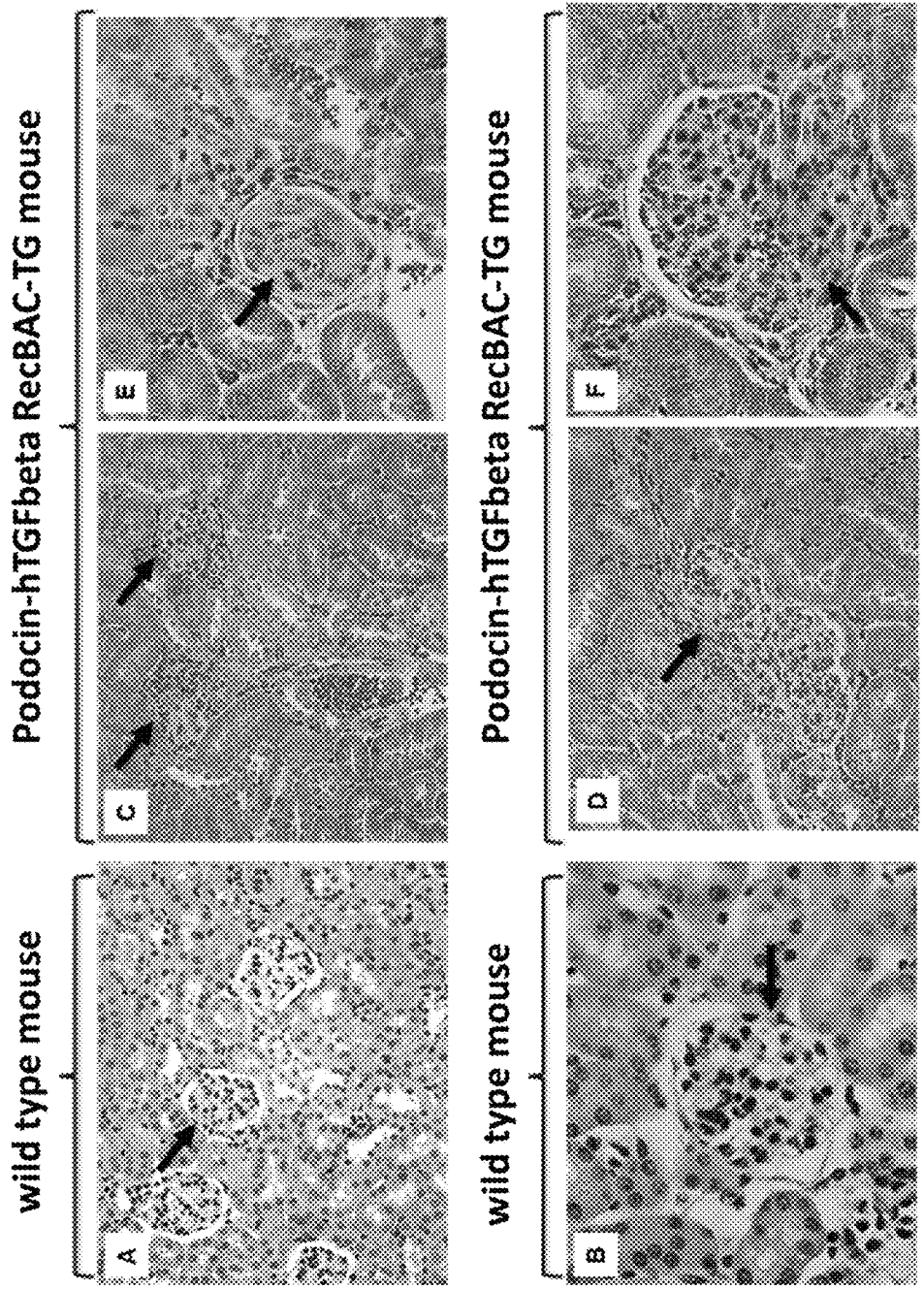

FIG. 7 shows photomicrographs showing kidney histology (Hematoxilin-Eosin staining) of wild-type mouse and mouse Podocin-human TGFβ1 RecBAC-TG mouse. The glomerulus of the wild type mouse (A, B) shows normal findings. Podocin-human TGFβ1 RecBAC-TG mouse showed glomerular dysfunction (C, D), glomerular fibrosis (E) and renal stromal fibrosis (F).

Figure 8:
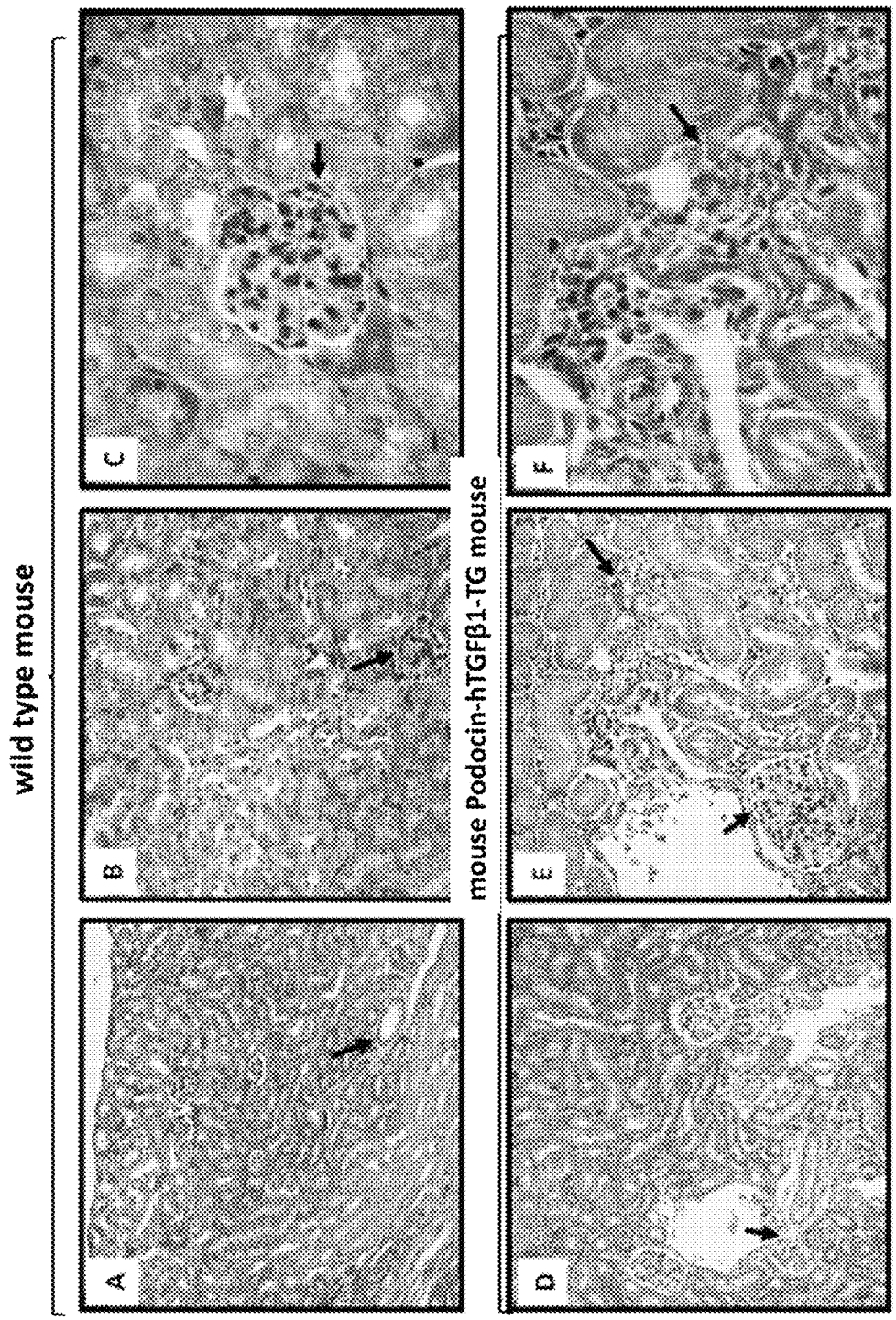

FIG. 8 shows photomicrographs showing collagen deposition (Masson's trichrome staining) in the kidney of wild type mouse and mouse Podocin-human TGFβ1 RecBAC-TG mouse. Collagen deposition of the kidney tissues of wild type mice is in the normal range (A, B, C), but collagen deposition of the kidney tissues of mouse Podocin-human TGFβ1 RecBAC-TG mice (D, E, F) is highly advanced.

Figure 9:
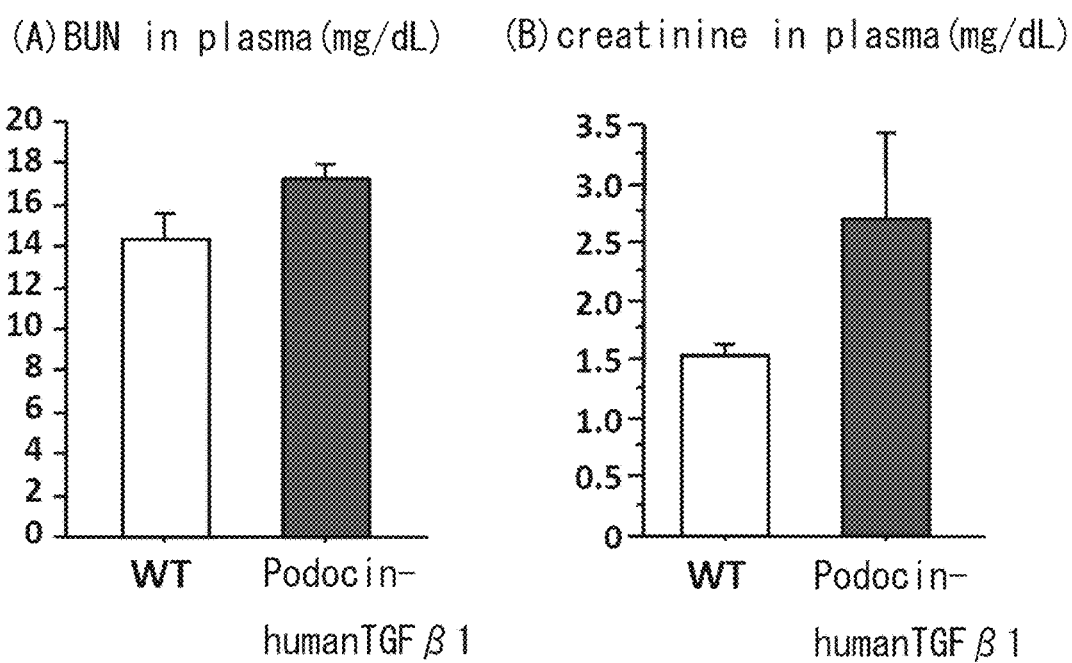

FIG. 9 is a graph showing the results of measuring BUN (A) and creatinine (B) in plasma of mouse Podocin-human/TGFβ1 RecBAC-TG mouse aged 16 weeks and those of wild type mouse. Both plasma concentrations were elevated in the mouse Podocin-human/TGFβ1 RecBAC-TG mice.

Figure 10:
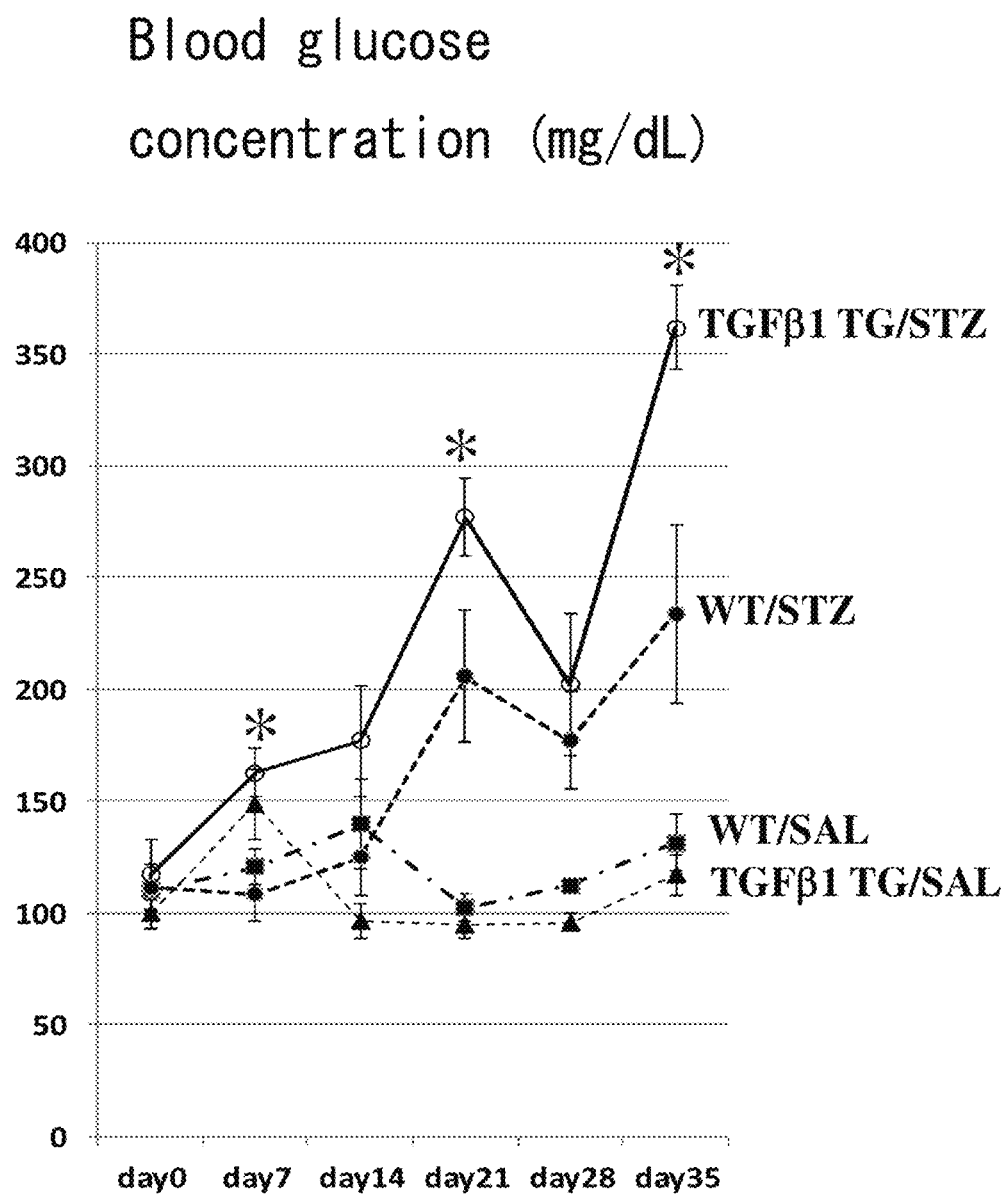

FIG. 10 is a graph showing the results of checking changes in the blood glucose concentration when streptozotocin (STZ) was administered to wild type mouse (WT) and mouse Podocin-human/TGFβ1 RecBAC-TG mouse (TGFβ1 TG).

Figure 11:
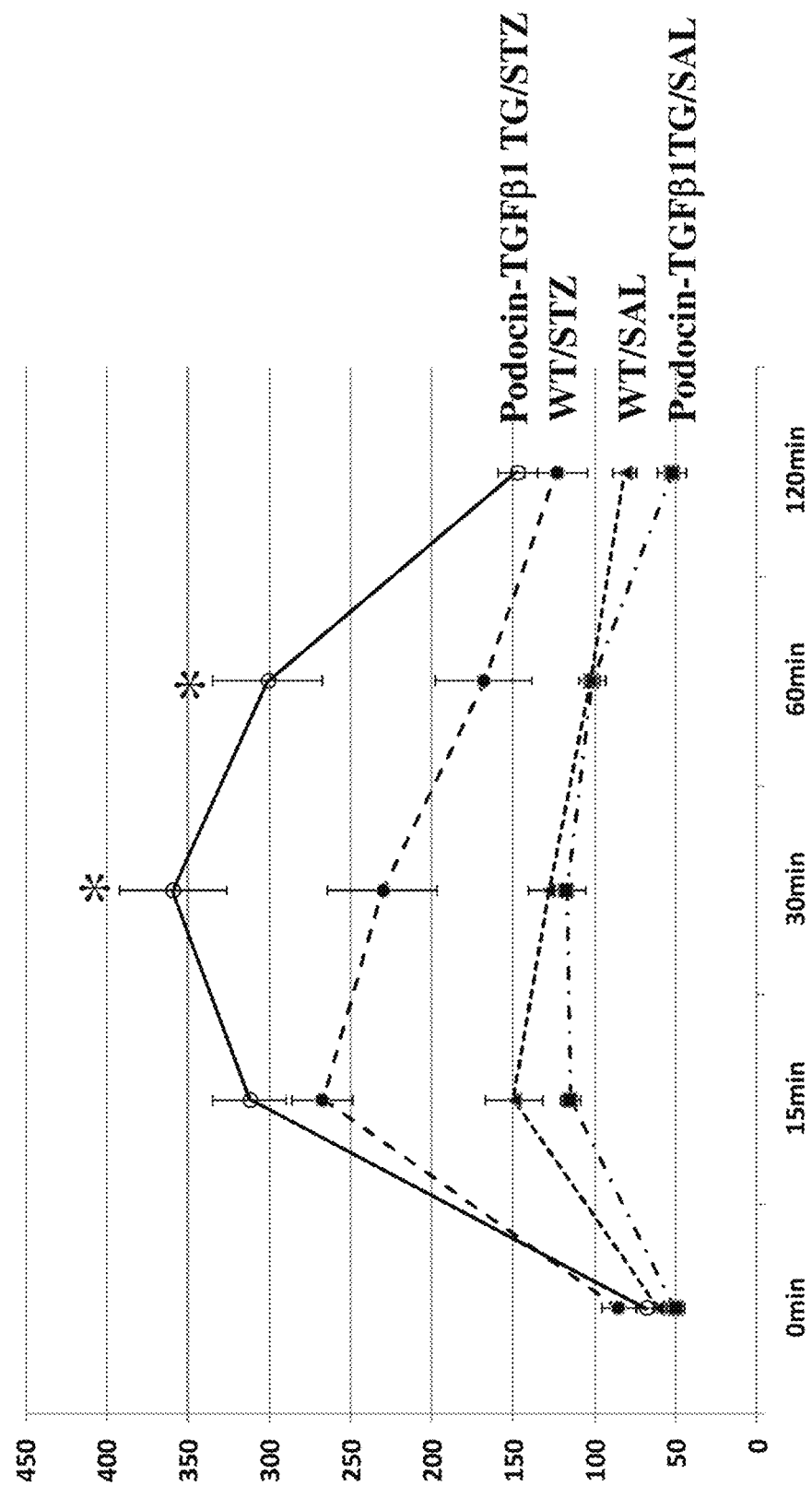

FIG. 11 is a graph showing the results of a glucose tolerance test.

Figure 12:
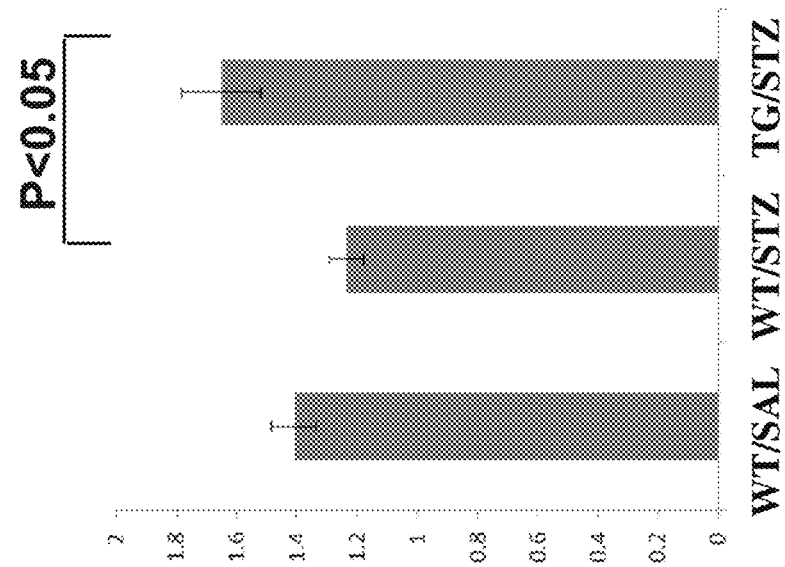
Figure 12:
Figure 12:

FIG. 12 is a CT photograph (A) of mouse Podocin-human/TGFβ1 RecBAC-TG mouse examined before and after administration of streptozotocin (STZ), and a graph (B) comparing kidney sizes before and after the test.

Figure 13:
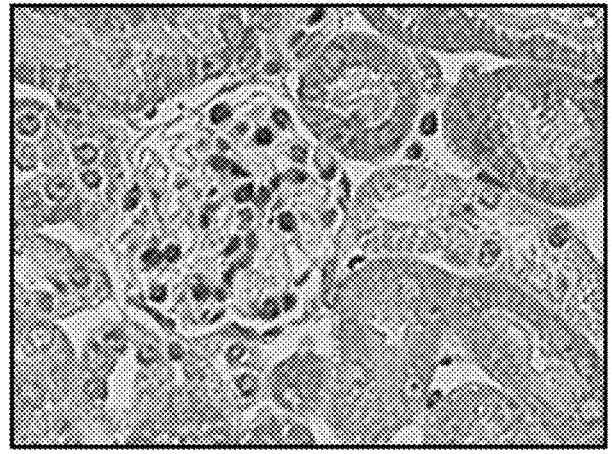
Figure 13:
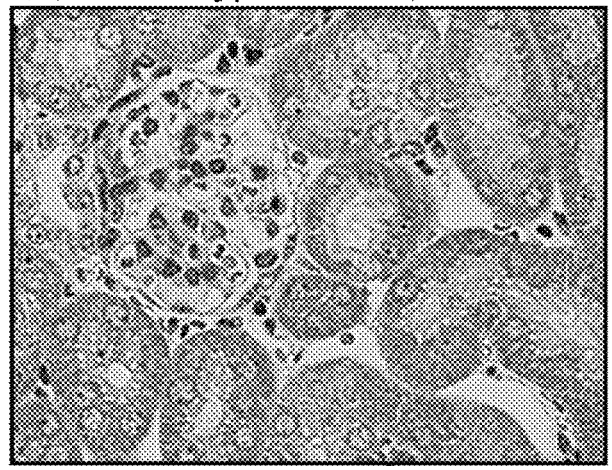
Figure 13:

FIG. 13 shows photomicrographs of the kidney tissue. A: a group to which salline was administered to a wild type mouse, B: a group to which STZ was administered to a wild type mouse, C: a group to which STZ was administered to a mouse Podocin-human/TGFβ1 RecBAC-TG mouse (TGFβ1 TG mouse), respectively.

Figure 14:
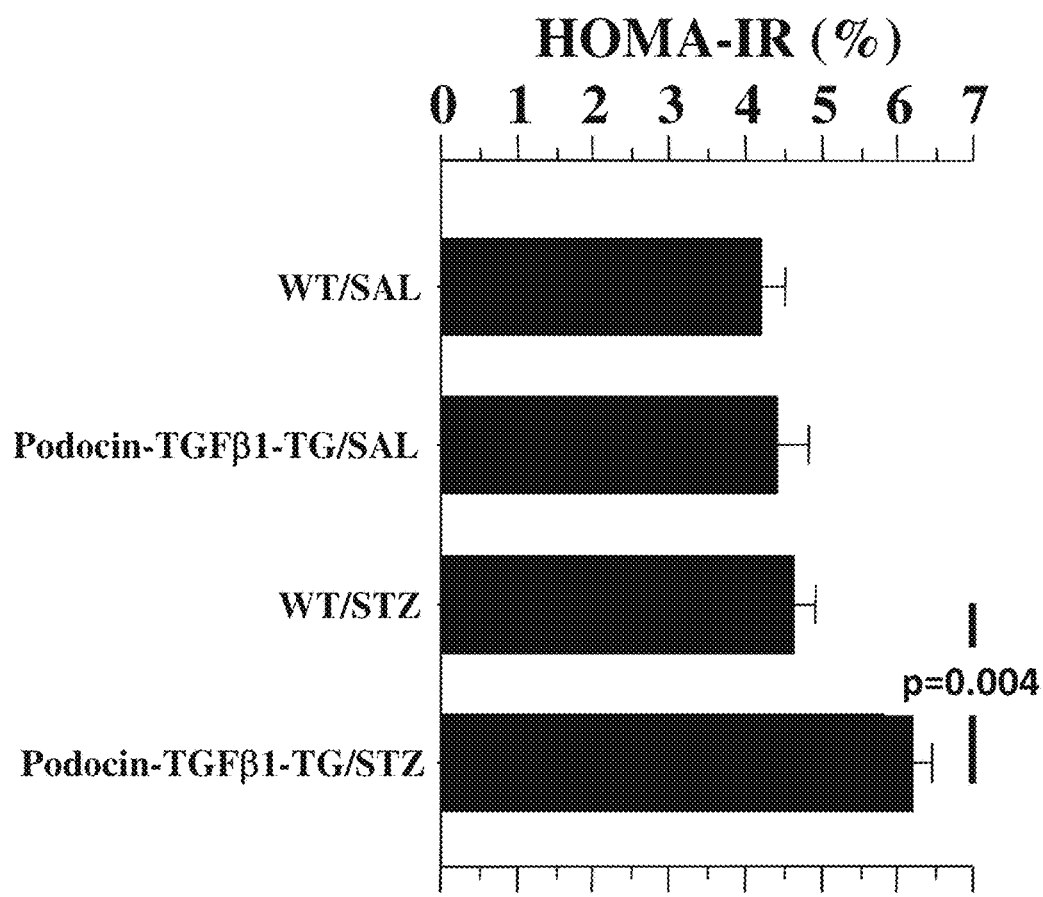

FIG. 14 is a bar graph showing the results of homeostasis model assessment (HOMA-IR) for each group of mice. In the graph, "WT/SAL" means the wild type mouse/saline administration group, "Podocin-TGFβ1-TG/SAL" means the transgenic mouse/physiological saline administration group, "WT/STZ" means the wild type mouse/STZ, "Podocin-TGFβ1-TG/STZ" means the transgenic mouse/STZ administration group, respectively.

Figure 15:
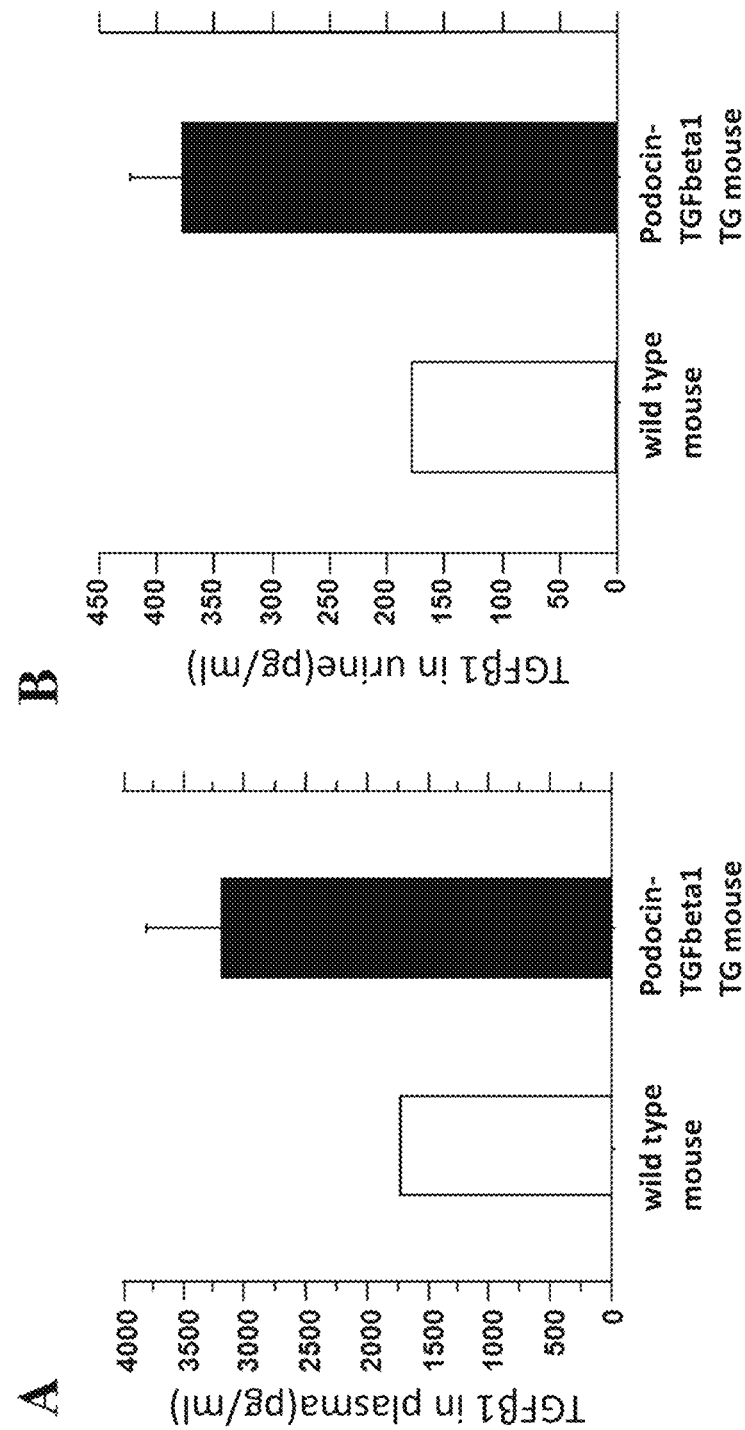

FIG. 15 is a graph showing the results of measurement of TGFβ1 concentration in mouse Podocin-human TGFβ1 RecBAC-TG mice. Human TGFβ1 concentrations in plasma (A) and urine (B) in Podocin-human TGFβ1 RecBAC-TG mice were higher than those in wild type mice.

Figure 16:
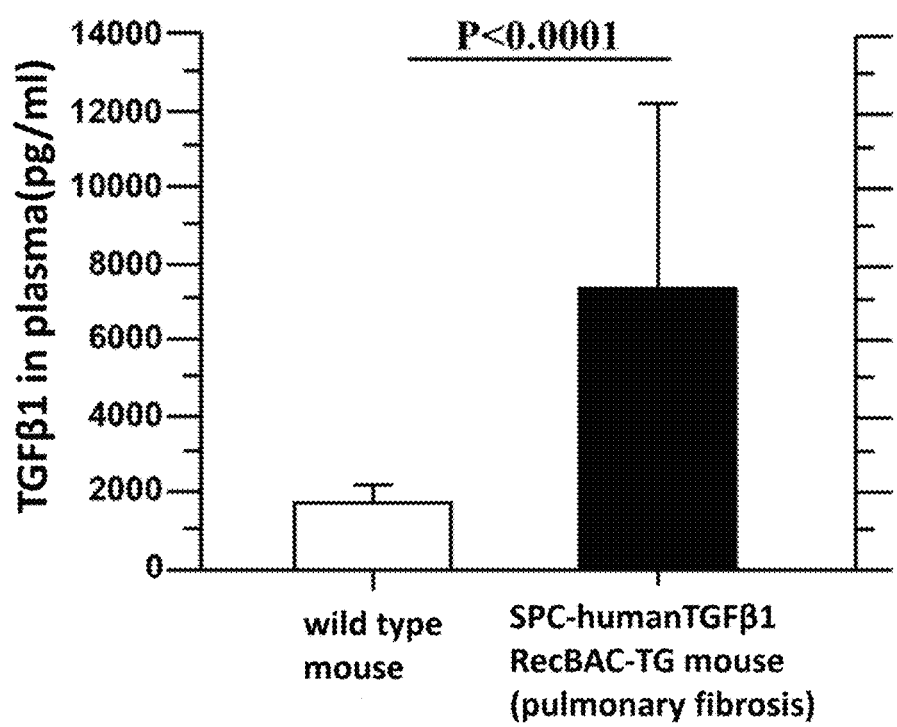
Figure 17:
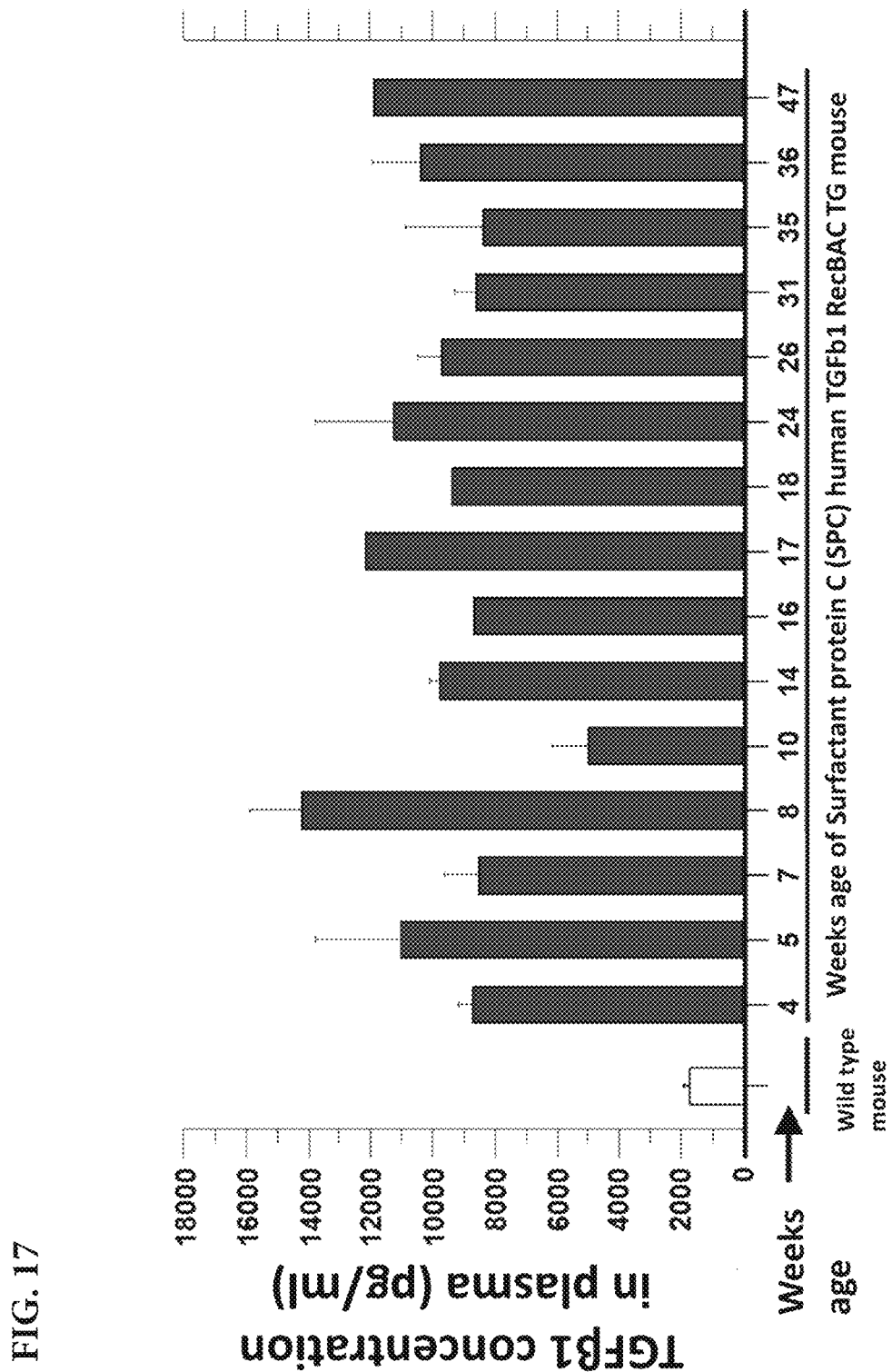

FIG. 16 is a graph showing the results of measurement of plasma TGFβ1 concentrations in mouse Surfactant protein C human TGFβ1 RecBAC-TG mice. Plasma human TGFβ1 concentrations in mouse Surfactant protein C-human TGFβ1 RecBAC-TG mice were significantly higher than those in wild type mice FIG. 17 is a graph showing the results of examining the relationship between the age of Surfactant protein C (SPC) human TGFβ1 RecBAC TG mice and the concentrations of TGFβ1 in plasma. The plasma TGFβ1 concentrations were kept high in mice above 10 weeks of age.

Figure 18:
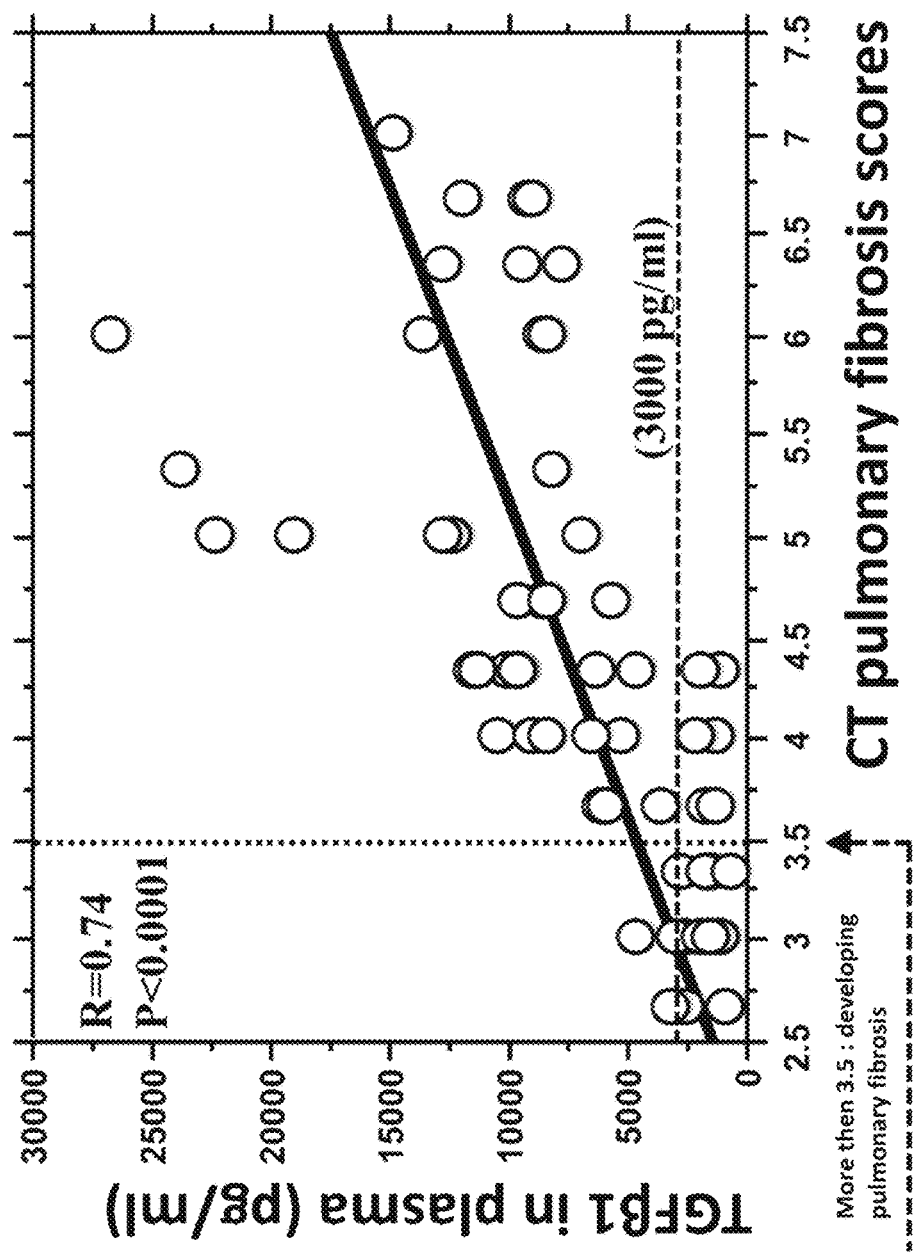

FIG. 18 is a graph showing the correlation between Computed tomography (CT) fibrosis scores and plasma TGFβ1 concentrations. CT pulmonary fibrosis scores and plasma TGFβ1 concentrations showed a significantly positive correlation. Mice with a plasma TGFβ1 concentration of 3000 pg/ml or more had a CT score of 3.5 or more. Mice showing plasma TGFβ1 concentrations with a cut-off value of 3000 pg/ml or more can be judged to be developing pulmonary fibrosis even without CT findings.

FIG. 19 is a graph showing the results of measurement of plasma TGFβ1 concentrations in pulmonary fibrosis patients and healthy subjects. (A) shows the average value, and (B) shows the whole individual values. (A) Plasma TGFβ1 concentrations in pulmonary fibrosis patients were significantly higher than those in healthy subjects. (B) Plasma TGFβ1 concentrations in some pulmonary fibrosis patients were higher than those in healthy subjects, and those in other pulmonary fibrosis patients were equal to those in healthy subjects.

DETAILED DESCRIPTION

Next, embodiments of the present invention will be explained with reference to the Figures and table. The technical scope of the present invention is not limited by these embodiments and can be carried out in various forms without changing the gist of the invention.

<Preparation of Human TGF Beta 1-BAC Transgenic Mouse>

1. Data of Human TGF Beta 1 Gene and Mouse Podocin Gene, and Search for Genomic Clones As a result of searching for mouse genomic DNA sequences based on the mouse Podocin cDNA sequence and 2. Construction of Recombinant BAC Clone of Mouse Podocin Gene and Human TGFβ1 Gene Using the active homologous recombination reaction in the construction of *E. coli*, Red/ET Recombination Technology (Non-Patent Document 3), we constructed a recombinant BAC clone of Podocin-human TGFβ1 RecBAC from BAC clone containing Podocin gene and TGFβ gene.

As shown in Table 1, the sequence of intron 1 of the human TGFβ1 gene, the sequences of both ends of the genomic DNA sequences from the translation initiation codon to the stop codon of human TGFβ gene, and the DNA sequences of 3'-side and 5' side of genomic translation initiation codon to the stop codon of Podocin genes of mouse BAC clone were used as the key sequence for the active homologous recombination reaction in *E. coli*.

TABLE 1

| Key Sequence | Position | Genomic Sequence (Sequence No. 1, to No. 6) |
|---|---|---|
| TGFβ1-H1 | Start cdor cf human TGFbeta-gene | [5']ATGCCGCCCTCCGGGCTGCGGCTGCTGCCGCTGCT[3'] |
| TGFβ1-H2 | Stop codon of human TGFbeta-gene | [5']CAACATGATCGTGCGCTCCTGCAAGTGCAGCTGA[3'] |
| TGFβ1-H3 | Rpsl-kan insertion site, 5'-side | [5']aggcgctggagaaagttgacccagagcttg[3'] |
| TGFβ1-H4 | Rpsl-kan insertion site, 3'-side | [5']ccttcttgaatctttccacctcaggacccc[3'] |
| Podocin-H5 | 5'UTR of mouse Podocin-gene | [5']gctGGGGCTGCGACTCTGCCAGCAGCTGGCTCCGGGGTTGCACCGCTGCATTGAGA[3'] |
| Podocin-H6 | 3'UTR of mouse Podocin-gene | [5']GCGAATGGGCAAAGGCTGTGTGAATCTGCCATATAAAGCCACATCCCTGAGAGAGG[3'] |

NM_130456, mouse Podocin gene was present in a region of chromosome 1. When the cDNA sequence of the mouse Podocin gene and the mouse genomic sequence were aligned, it became clear that the coding region of the mouse Podocin gene includes eight exons in the genomic sequence in 17 kb region.

After searching for a BAC clone encoding mouse Podocin locus, the genomic DNA sequence of mouse Podocin locus was contained in RP23-5701. The BAC clone contained a 225 kb of chromosome 1 with mouse Podocin locus, 5' genomic sequence upstream of the 69 kb, and 3' genomic sequence downstream of the 139 kb (FIG. 2). Based upon this genetic information, we thought that the BAC clone of 225 kb, RP23-5701, contained all expression control sequences that drive the Podocin gene. It was reasonable that the clone was utilized to construct an expression vector for human TGFβ1 gene (FIG. 1(A)).

As a result of searching for human genomic DNA sequences based on the cDNA sequence of human TGFβ1 gene, NM_000660, human TGFβ gene was found in the 19q13.1 region of chromosome 19. Comparing the cDNA sequence of human TGFβ with human genome sequence, the coding region of the human TGFβ1 gene was shown to encode seven exons in the genomic sequence spanning 23 kb.

Figure 1:
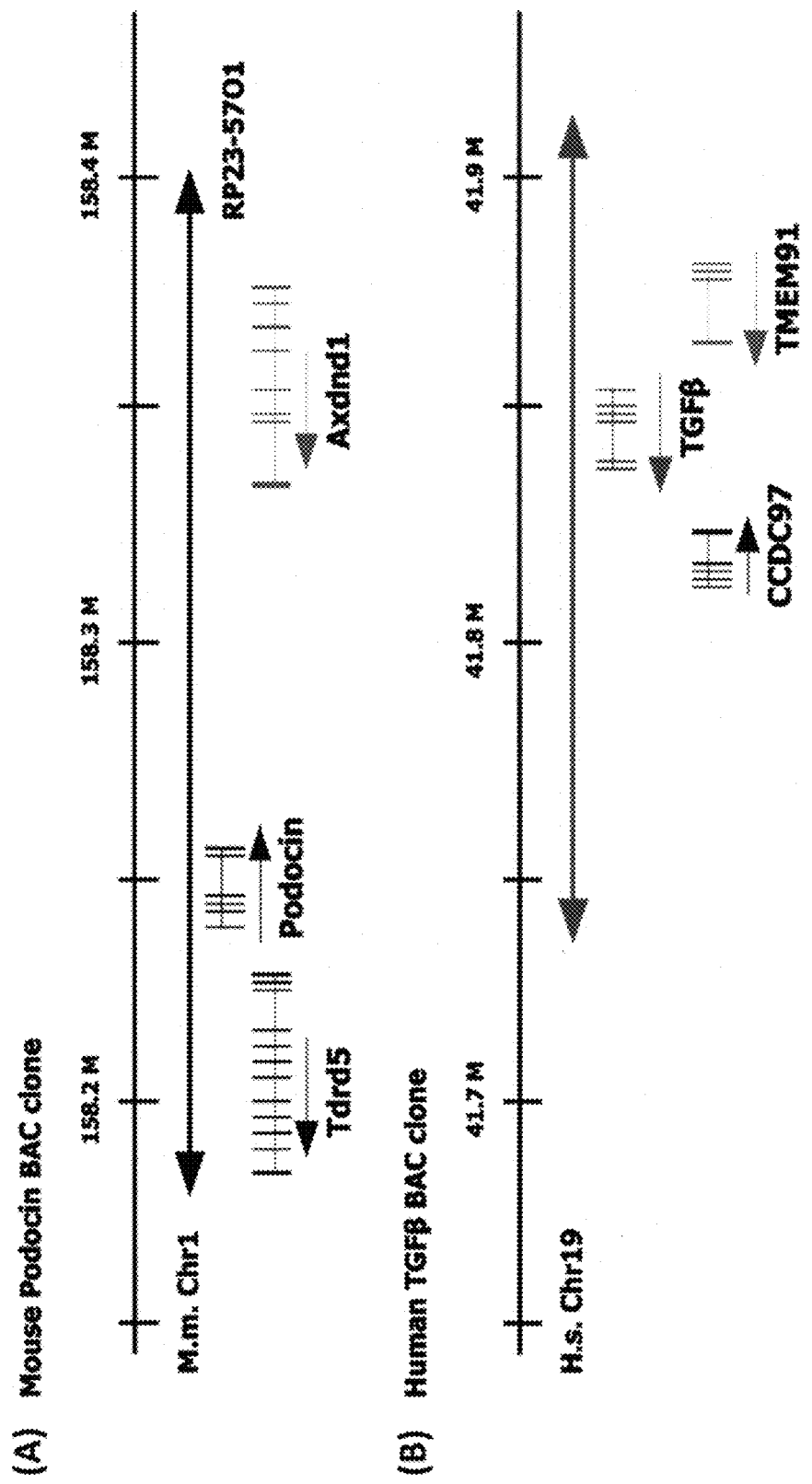
FIG. 1 illustrates a method for searching information and genome clone of human TGFβ1 gene and mouse Podocin gene.
Figure 2:
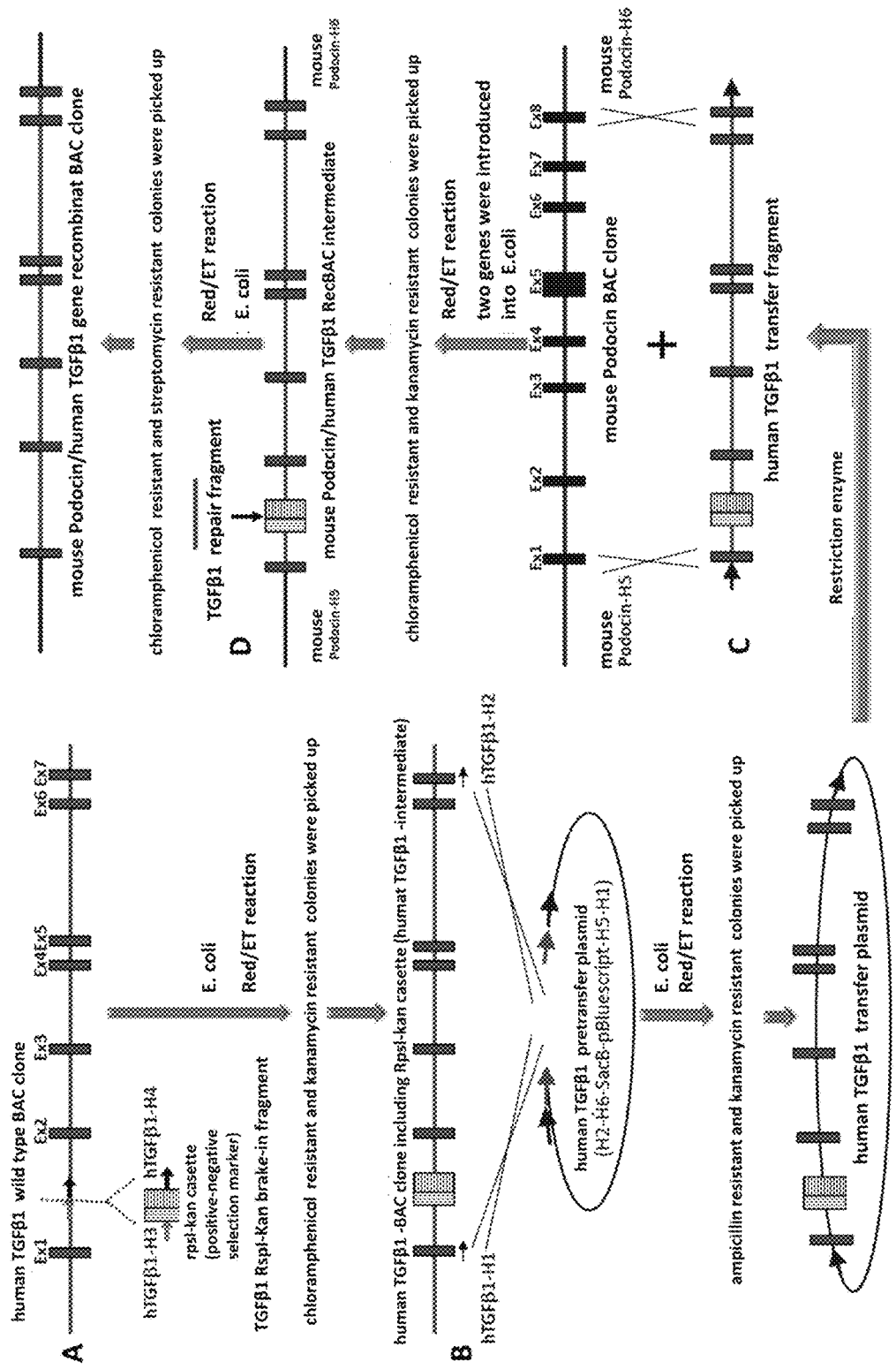
FIG. 2 illustrates a diagram for explaining the construction method of the recombinant BAC clones of the mouse Podocin gene and human TGFβ1 gene.

After searching for BAC clones encoding the human TGFβ gene locus, RP11-638N16 size of 194.7 kb was found to contain all of the genomic DNA sequence of the human TGFβ1 gene locus (FIG. 1(B)).

The DNA fragment contained TGFβ1-113 sequence, Rpsl-kan and TGFβ1-114 in tandem arrays was constructed by PCR using LA-Taq (Takara Bio) (TGFβ1 Rpsl-Kan break-fragment), in order to insert the positive/negative selection marker cassette (Rpsl-kan corresponding to the selected cassette of the present invention) in intron 1 of TGFβ1 gene of human BAC clone (FIG. 2A). A human BAC clone containing the TGFβ1 locus and a TGFβ1 Rpsl-Kan break-in fragment were introduced into an *Escherichia coli* strain with the ability of the Red/ET reaction, to induce a Red/ET reaction in the host *E. coli*, and chloramphenicol resistant and kanamycin resistant colonies were picked up to screen recombinant BAC clones in which the TGFβ1 Rpsl-kan break-in fragment was inserted into intron 1 of the TGFβ1 locus (human TGFβ1 Intermediate: recombination step for preparing a gene for selection) (FIG. 2A).

With using human TGFβ1 Intermediate, in order to subclone the genomic DNA sequence of the human TGFβ1 gene into which the Rpsl-kan cassette was inserted to a plasmid vector, a DNA cassette in which H2-H6-SacBp and Bluescript-H5-H1 were tandemly connected was constructed (human TGFβ1 transfer plasmid) (FIG. 2B). In the same manner as described above, human TGFβ1 intermediate and linearized TGFβ1 pre transfer plasmid were introduced into the *E. coli* strain with the ability of Red/ET reactions, to induce a Red/ET reaction in the host *E. coli*, and ampicillin resistant and kanamycin-resistant colonies were picked up to screen plasmids in which the Rpsl-kan cassette was inserted into a genomic DNA sequence of the human TGFβ1 gene (human TGFβ1 transfer plasmid) (FIG. 2B).

Then, the genomic DNA sequence of the human TGFβ1 gene, which possesses an H5 sequence and an H6 sequence derived from the mouse genome sequence at the two ends thereof and had the Rpsl-kan cassette inserted therein, was excised from this human TGFβ1 transfer plasmid by performing a restriction enzyme reaction (human TGFβ1 transfer fragment: Creating and modification step of modified human TGFβ1 gene fragment) (FIG. 2C). In the same manner as described above, the mouse Podocin BAC clone and the human TGFβ1 transfer fragment were introduced into an E. coli strain having the Red/ET reaction capability; by inducing the Red/ET reaction in the host E. coli and by picking up chloramphenicol resistant and kanamycin resistant colonies of recombinant BAC clones of the mouse Podocin-human TGFβ1 gene, in which the genomic DNA sequence from the translation initiation codon of the human TGFβ1 transfer fragment to the stop codon accurately replaced the genomic DNA sequence from the translation initiation codon of the mouse Podocin gene to the stop codon, recombinant BAC clones were screened (murine Podocin-human TGFβ1 RecBAC Intermediate: step for preparing a Podocin-human TGFβ1 gene fragment for selection) (FIG. 2C). As shown in Podocin-H5 and Podocin-H6, genome sequences having 56 bases were designed and produced as homology arms at the time that the human TGFβ1 transfer fragment was introduced into the mouse Podocin BAC clones.

H5 and H6 are each DNA primers having a length of 56 bases and they have a greater number of bases than when typical PCR reactions are performed. To create the transgenic mouse of the present embodiment, the number of bases of H5 and H6 is one of the important constituent requirements. If the number of bases of H5 and H6 is too short, an hTGF β1-expressing transgenic mouse could not be prepared. Therefore, the number of bases of H5 and H6 are from 50 bases to 60 bases, preferably from 52 bases to 60 bases, and even more preferably from 54 bases to 58 bases.

Figure 3:
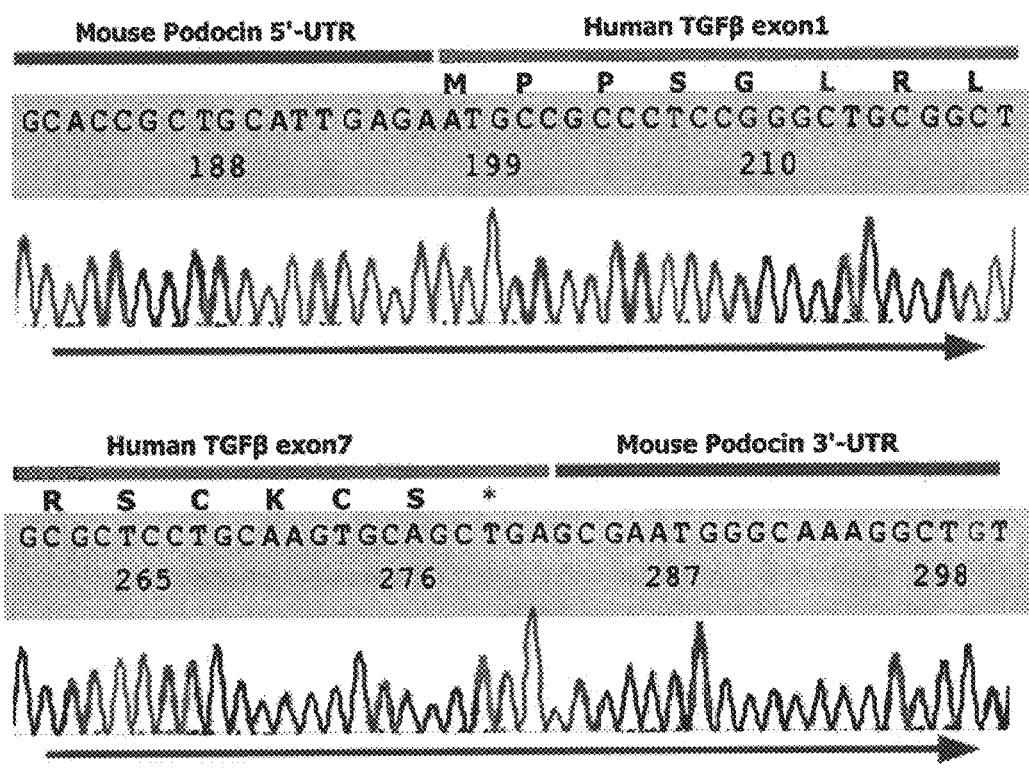
FIG. 3 illustrates the results of confirming the genomic DNA sequence of H1 to H6 conjugated with Red/ET reactions.

Finally, the intron 1 sequence of the human TGFβ1 gene locus was amplified by PCR, and it was used as the DNA sequence for removing Rpsl-Kan, which had been inserted into intron 1 of the human TGFβ1 gene by performing negative selection (human TGFβ1 repair fragment) (FIG. 2D). In the same manner as described above, the mouse Podocin-human TGFβ1 RecBAC Intermediate and the human TGFβ1 repair fragment were introduced into an E. coli strain having the Red/ET reaction capability; by inducing the Red/ET reaction in the host E. coli and then by picking up chloramphenicol resistant and streptomycin resistant colonies of recombinant BAC clones of the mouse Podocin-human TGFβ1 gene, in which the genomic DNA sequence from the translation initiation codon of the human TGFβ1 gene to the stop codon accurately replaced the genomic DNA sequence from the translation initiation codon of the mouse Podocin gene to the stop codon, recombinant BAC clones having the mouse Podocin-human TGFβ1 gene were screened (Podocin-human TGFβ1 RecBAC: a step for preparing a Podocin-TGFβ1 BAC transgenic construct) (FIG. 2D). The genomic DNA sequence of H1 to H6 joined by the Red/ET reaction was confirmed by sequence analysis (FIG. 3).

3. Purification of Mouse Podocin-Human TGFβ1 RecBAC Recombinant Expression Construct DH10B cells transformed by recombinant BAC clone which contained mouse Podocin-human TGFβ1 RecBAC recombinant expression construct were cloned on LB agar medium containing chloramphenicol. The single colony of DH10B was picked up and shaking cultured overnight in liquid culture medium. The mouse Podocin-human TGFβ1 RecBAC recombination BAC clone was purified according to modified Abe et al, method (Non-Patent Document 4) with a plasmid extraction kit (Macchi Lee Nagel Inc., Nucleobond BAC100 kit) and was reacted with PI-SceI at 37° C. for 16 hours.

Figure 4:
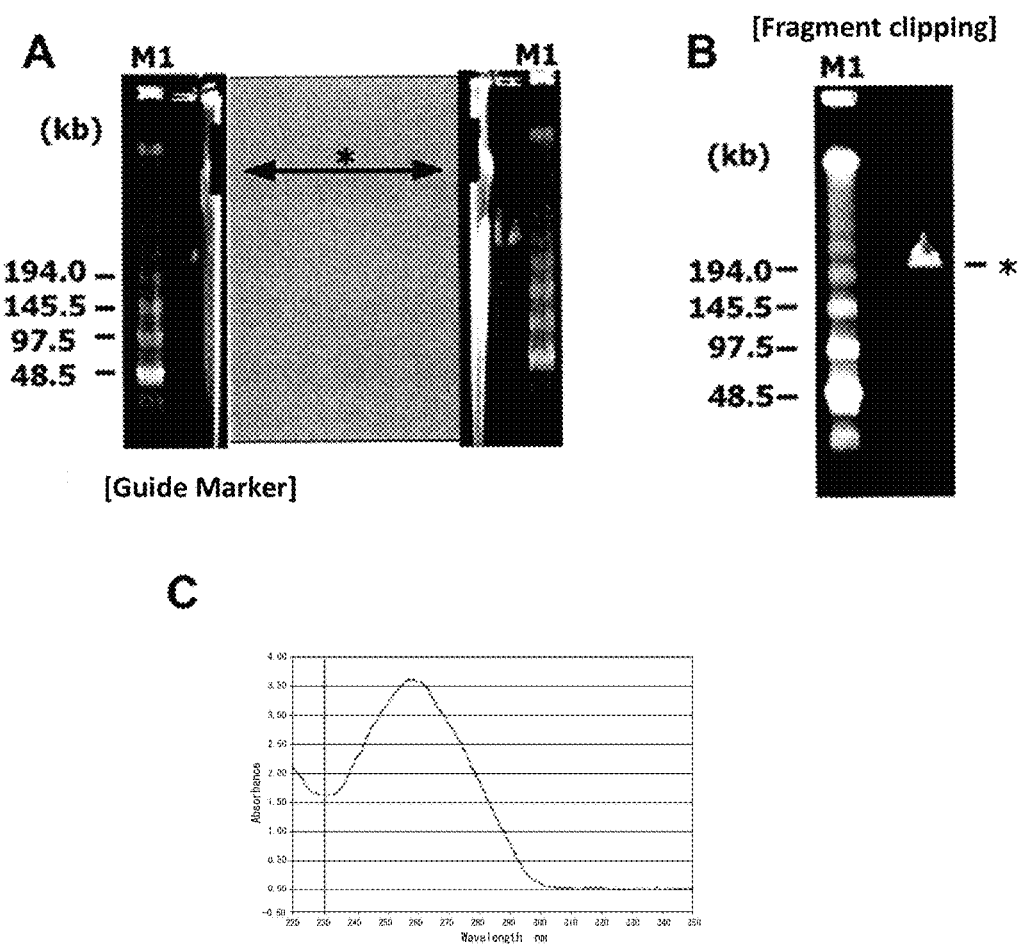
FIG. 4 shows the results of purification of the mouse Podocin-human TGFβ RecBAC expression construct. (A) Gel photographs: The expression construct linearized with PI-SceI was isolated by pulsed field electrophoresis system. Only samples that were applied as a guide markers on both ends of the gel were visualized by gel photograph. The gel containing the expression construct isolated in agarose gel were cut without UV irradiation. (B) Gel photographs: the DNA fragment which was purified by electroelution and dialysis was applied to a pulse field electrophoresis, and was confirmed that the long DNA fragment was divided without fragmentation. (C) Graph of the results of DNA concentration by NanoDrop Spectrophotometer: Marker in the figure, M1 is the NEB Low Range PFG marker.

To obtain an expression construct for a transgenic mouse, the genomic BAC clone was digested with PI-SceI and separated by pulsed-field electrophoresis. Long DNA fragments containing the expression construct with 150 kb to 200 kb were detected. These DNA fragments were cut out from the gel avoiding damage by UV irradiation, electroeluted and purified by dialysis. The purified expression construct was examined for the purity and concentration by 1% agarose gel electrophoresis for analysis. It was confirmed that the long expression construct had been recovered with enough purity. The DNA concentration was 181.2 ng/μl. It was sufficient to provide a transgenic mouse (FIG. 4A, B, C).

4. Injection of Mouse Podocin-Human TGFβ1 RecBAC Expression Construct into Mouse Embryo Pregnant male serum gonadotropin (PMSG) and human chorionic gonadotropin (hCG) were administered to female C57BL/6J mice to induce superovulation. The mice were crossed with the same strain of male mice, and taken fertilized eggs. The male nucleus of pronuclear stage embryos of C57BL/6J mice were injected with purified mouse Podocin-human TGFβ1 RecBAC expression construct directly using the micromanipulator. The DNA-injected embryo was transplanted into the oviduct of an embryo female mouse induced pseudopregnancy (a step for obtaining a transgenic mouse).

As described before, fertilized eggs were collected from the superovalated female mice administered PMSG and hCG. The mouse Podocin-human TGFβ1 RecBAC expression construct was introduced into the fertilized eggs by a microinjection method. The fertilized eggs introduced expression constructs were transplanted into the oviducts of pseudopregnant treated mice. A total of 407 fertilized eggs were collected from C57BL/6J female mice that underwent superovulation induction and mated. A total of 392 fertilized eggs were injected with the mouse Podocin-human TGFβ1 RecBAC expression construct by microinjection method. The mouse-fertilized-eggs received microinjection were observed by microscope. The damage by the injection operation was small. A total of 360 fertilized eggs remained stable even after microinjection. Of these fertilized eggs, 344 of fertilized eggs injected by the expression construct without damage were transplanted into pseudopregnant treated mice.

Figure 5:
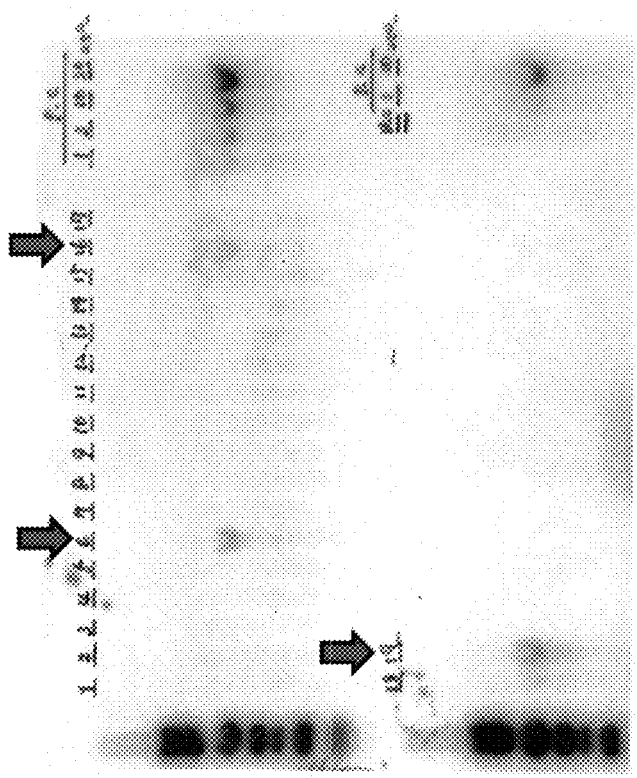
FIG. 5 are gel photographs showing the results of identification of Podocin-human TGFβ RecBAC transgenic mouse founders by Southern hybridization.
Figure 5:
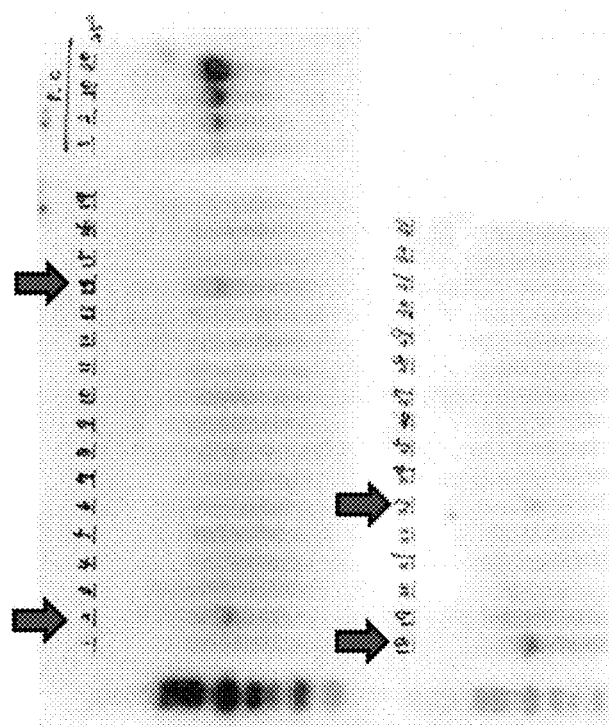

5. Southern Screening of Mouse Podocin-Human TGFβ RecBAC Transgenic Mouse Founder Founder candidates of the transgenic mice were obtained from fertilized eggs of C57BL/6J mice into which the mouse Podocin-human TGFβ1 RecBAC expression construct was introduced by a microinjection method. Southern analysis was performed to identify founder individuals. Expression constructs were injected into a total of 392 fertilized eggs, and a total of 344 injected embryos were transplanted into pseudopregnant mice and spontaneously delivered. A total of 52 mouse origins were obtained. All 52 mice were grown until weaning. The number of progeny and weaning from the early embryo into which the mouse Podocin-human TGFβ1 RecBAC expression construct was introduced was good. From these data, we confirmed that there was no adverse effect on the development and differentiation of mouse embryos by injecting expression constructs. Eight animals which had been transfected with the mouse Podocin-human TGFβ1 RecBAC expression construct were identified as a transgenic mouse founder by the hybridization of the genomic DNA fragments extracted from the offspring of the founder candidate transgenic mice with [32P] labeled probe identified. The copy number of the expression construct introduced into the transgenic mouse founder was 1 copy to 3 copies (FIG. 5). The southern blot in which genomic DNA fragments of the candidates of transgenic mouse founders were transferred was incubated with [32 P] labeled Podocin-human TGFβ RecBAC by random prime method, and hybridized. After the nylon membrane was washed to remove non-specifically bound radioactive probe, specifically binding fragments were detected with autoradiography. Markers in the figure are M1: NEB, 1 KB ladder.

6. Reverse Transcriptase Polymerase Chain Reaction (RT-PCR)

Reverse transcriptase PCR (RT-PCR) was performed to examine the expression level of human TGFβ1 gene in each tissue of human TGFβ1 TG mice. Total RNAs were extracted from each tissue with TRIZOL (Invitrogen, Carlsbad, Calif.). Sequences of the primers used for RT-PCR were as follows;

Human TGFβ1, forward 5'-AAG ACT ATC GAC ATG GAG CTG G-3' (SEQ ID NO: 7) and, reverse 5'-GTA TCG CCA GGA ATT GTT GCT G-3' (SEQ ID NO: 8); human GAPDH, forward 5'-CCA CCC ATG GCA AAT TCC ATG GCA-3' (SEQ ID NO: 9) and reverse 5'-TCT AGA CGG CAG GTC AGG TCC ACC-3' (SEQ ID NO: 10); mouse GAPDH, forward 5'-CCC TTA TTG ACC TCA ACT ACA TGG T-3' (SEQ ID NO: 11) and reverse 5'-GAG GGG CCA TCC ACA GTC TTC TG-3' (SEQ ID NO: 12). All PCRs were performed in a state before plateau. PCR products were electrophoresed on a 2% agarose gel, and observed by ultraviolet light after staining the bands with ethidium bromide. Expression of mouse TGFβ1 was observed in almost all organs. Meanwhile, expression of human TGFβ1 was observed only in the kidney (FIG. 6).

7. Histological Examination of Kidney

After mice were sacrificed, the renal circulation was washed with saline. Kidneys were removed from the mouse. The kidney was perfused with formalin (10% neutral buffer), inflated with gas, fixed in formalin for 24 hours, and embedded in paraffin. Sections for tissue examination with a thickness of 5um were prepared, paraffin was removed, and washed several times with saline-phosphate buffer. Tissue sections were treated with hematoxylin/eosin staining method. Histological examination of the kidneys was performed using an Olympus BX50 microscope equipped with a Olympus DP70 digital camera. Glomerular of wild-type mice showed normal findings. Glomerular degeneration, glomerular fibrosis and renal interstitial fibrosis were observed in the kidney of mouse Podocin-human/TGFβ1 RecBAC-TG mice (FIG. 7). Glomerulus of wild-type mice showed normal findings (A, B). Atrophy of the glomerulus (C, D), glomerular fibrosis (E) and fibrosis of the renal interstitium (F) in Podocin-human TGFβ1 RecBAC-TG mice were observed.

To examine the extent of collagen deposition in the kidney tissue, tissue sections were treated with Masson trichrome staining method. As a result, collagen deposition in renal tissue was normal range in wild-type mice (A, B, C), but was high in Podocin-human TGFβ1 RecBAC-TG mice (D, E, F) (FIG. 8).

<Test to Confirm that the Mouse is Susceptible to Diabetes>

As a result of measuring BUN and creatinine in the blood plasma, for plasma concentrations of mouse Podocin-human/TGFβ1 RecBAC-TG mice (transgenic mice) were all increased, it wad found that renal dysfunction had occurred from 16 weeks of age (FIG. 9). Therefore, a test was conducted as to whether or not the renal dysfunction of the transgenic mouse was likely to progress due to diabetes. At that time, it was tested whether diabetes likely to develop or not.

1. Test Method (i) Streptozotocin (STZ: 40 mg/kg) was administered to wild-type mice (n=4) and mouse Podocin-human/TGFβ1 RecBAC-TG mice (n=5) once a day for 4 days to induce diabetes. As a control, saline (saline) was administered to wild-type mice (n=3) and mouse Podocin-person/TGFβ1 RecBAC-TG mice (n=5).

Blood samples were collected from each mouse before the start of the test (day0), the 7th day (day7), the 14th day (day14), the 21th day (day21), the 28th day (day28) and the 35th day (day35) after the start of the test, and the blood sugar levels were examined.

(ii) Glucose tolerance test was conducted using mice on the 28th day after the start of the test. One g/kg of glucose was administered intraperitoneally to mice, blood glucose levels were measured after 15, 30, 60 and 120 minutes from the glucose administration.

(iii) After the test, each mouse was performed CT examination to examine the degree of renal disorder. In addition, the status of kidney tissue was examined using a microscope.

(iv) HOMA-IR (homeostasis model assessment) was examined for each group of mice using the data of fasting blood glucose level (i) and (ii).

2. Results

Mice blood glucose levels of each group were shown in FIG. 10. No statistically significant difference in the blood glucose levels were observed between in wild-type (WT/SAL) and in transgenic mice (TGFβ1 TG/SAL). On the other hand, although significant difference was not observed in the group administered with STZ, the blood glucose levels in wild-type (WT/STZ) rose. In the transgenic mice (TGFβ1 TG/SAL), significantly ($p<0.05$) increased glucose levels were found.

The results of glucose tolerance test were shown in FIG. 11. Blood glucose levels in the STZ-administered group compared to those in the control (SAL) group were elevated. In particular, blood glucose levels in the transgenic mice (TGFβ1 TG/SAL) were increased significantly at 30 and 60 minutes after glucose administration ($p<0.05$). As a result, transgenic mice were found to have developed diabetes at 4 weeks of age.

In FIG. 12A, the CT images of the transgenic mouse before and after STZ administration were shown. In FIG. 12B, the size of the kidney before and after the test was shown. The kidney of the transgenic mice (TG) became significantly larger (about 1.6 times) by the administration of STZ.

FIG. 13 showed the results of observation under a microscope renal tissue. In wild type mice, no significant change was observed by administration of STZ (FIG. 13A, FIG. 13B). In transgenic mice, the pathogenesis of sclerosis was observed by administration of STZ (FIG. 13C).

Thus, mouse Podocin-human/TGFβ1 RecBAC-TG mice were found to be prone to diabetes than wild-type mice by administration of streptozotocin (STZ).

HOMA-IR in four groups (wild type mice/saline-treated group, transgenic mice/saline-treated group, wild-type mice/STZ administration group, and transgenic mice/STZ administration group) were shown in FIG. 14. HOMA-IR were obtained based on the formula following.

HOMA-IR=fasting blood insulin concentration (μU/mL)×fasting blood glucose level (mg/dL)×1/405

In the transgenic mice/STZ administration group, HOMA-IR was significantly increased. The data showed that TGFβ1 was highly expressed in the transgenic mice, the mice acquired insulin resistance, and easily suffer from type II diabetes mellitus.

<Importance of TGFβ1 Measurement as a Biomarker>

By the way, TGFβ1 is known to play an important role for the pathogenesis of organ fibrosis such as pulmonary fibrosis, glomerular sclerosis and liver cirrhosis. Among such fibrosis patients, some patterns of examples have been reported showing the varying clinical outcomes. This is called a clinical phenotype of fibrosis (phenotype).

However, it has not been fully elucidated association between TGFβ1 concentrations in plasma and TGFβ1 type of fibrosis. Therefore, in this embodiment, we can indicate the patterns of TGFβ1 type of fibrosis by measuring the TGFβ1 in plasma.

1. Study of TGFβ1 Concentrations in Mouse Podocin-Human TGFβ1 Rec BAC TG Mice

TGFβ1 concentrations were measured using commercially available ELISA kits (BD Biosciences Pharmingen, San Diego, Calif.) according to the manual. The concentrations of human TGFβ1 in the blood and urine in mouse Podocin-human TGFβ1 Rec BAC TG mice showed significantly higher compared to those in wild-type mice (FIG. 15).

2. Study of TGFβ1 Concentrations of Mouse Surfactant Protein C/Human TGFβ1 Rec BAC TG Mice The present inventors have established transgenic mice expressing TGFβ1 in a specific organ with incorporating various ideas. In established transgenic mice by the present inventors, there is a transgenic mouse (mouse Surfactant protein C/human TGFβ1 Rec BAC TG mice) specifically expressing human TGFβ1 in the lung.

Therefore, we examined the relationship between plasma TGFβ1 concentrations and pulmonary fibrosis using the transgenic mice. In mouse Surfactant protein C/human TGFβ1 Rec BAC TG mouse, human TGFβ1 concentrations in plasma showed significantly higher compared to those in wild-type mice (FIG. 16). Human TGFβ1 concentrations in plasma increase early (4 weeks old), and they were found to be hold at 10 weeks of age or more (FIG. 17).

3. Relationship TGFβ1 Concentrations and Micro CT (Computed Tomography) in Mouse Surfactant Protein C/Human TGFβ1 Rec BAC TG Mice Evaluation of pulmonary fibrosis in the mouse model was performed using micro CT. CT data were obtained using mice under anesthesia which were suppressed respiration by inhalation of isoflurane. CT findings of pulmonary fibrosis were scored from 1 to 8 and evaluated. There was a significant positive correlation between CT lung fibrosis score and plasma TGFβ1 concentrations. Mice with higher plasma concentrations of TGFβ1 than 3000 pg/ml (cut-off value) were observed 3.5 or more CT score (FIG. 18). Thus, mice with higher plasma concentrations of TGFβ1 than 3000 pg/ml can be determined with pulmonary fibrosis even without CT findings.

4. Study of Plasma TGFβ1 Concentrations in Fibrosis Patients

Figures 19A, 19B:
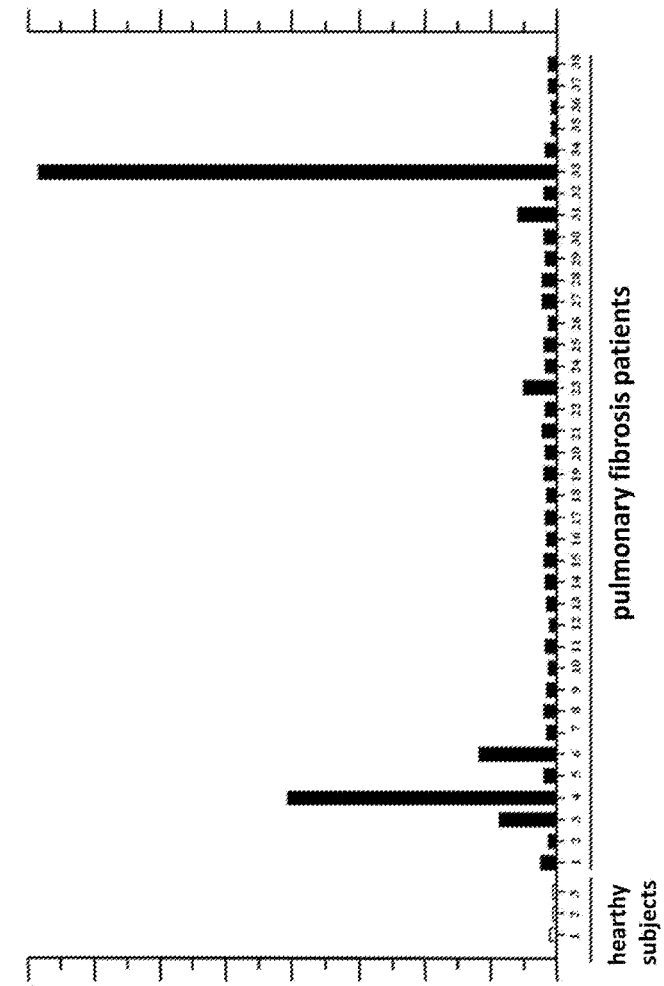

Next, we examined the relationship between the human lung fibrosis patients and plasma TGFβ1 concentrations. TGFβ1 concentrations in plasma were measured in patients with lung fibrosis (38 patients) and healthy subjects (3 subjects). TGFβ1 concentrations in patients with pulmonary fibrosis were significantly higher than those in normal subjects (FIG. 19(A)). To consider the plasma TGFβ1 concentrations of each case, some patients showed higher TGFβ1 concentrations, others showed lower TGFβ1 concentrations (FIG. 19(B)). Thus, the patients with high TGFβ1 concentrations were considered to be TGFβ1 type fibrosis (FIG. 19).

As shown in FIG. 7, 8, as kidney fibrosis progressed in mice Podocin-human TGFβ1 RecBAC-TG mice, as shown in FIG. 15A, the concentrations of human TGFβ1 in the blood rose approximately twice as compared to those in wild type mice. As shown in FIG. 15B, urinary human TGFβ1 concentrations, as compared to those in wild-type mice, showed increased about twice. As shown in FIG. 6, since human TGFβ1 was expressed especially in the kidney, it was considered that the elevation of human TGFβ1 concentrations in the blood and urine reflected kidney fibrosis. In this way, it was found that the concentration of human TGFβ1 in the blood and urine can be a marker reflecting kidney fibrosis.

Since TGFβ1 expression was increased in the renal glomerulus fibrosis, TGFβ1 was excreted in the urine from an early stage, so it reflected early fibrosis and may be useful as a marker for early diagnosis of fibrosis. Meanwhile, glomeruli were impaired by fibrosis, when the number of nephrons were reduced to decrease the TGFβ1 excretion in the urine, as a result, it was considered that the TGFβ1 concentrations in the blood would increase. Therefore, elevation of TGFβ1 in the blood may reflect the severity of fibrosis. In particular, in breeding mouse Podocin-human TGFβ1 RecBAC-TG mice, it is a model mouse that spontaneously develops kidney fibrosis, unlike wild type mouse diagnosis, so it can be an extremely effective index for confirming the timing of the onset of renal fibrosis. This makes it possible to efficiently confirm the onset of breeding mice, so it is easy to provide the mice to research institutions on renal fibrosis diseases. Similarly, in the breeding of mouse Surfactant protein C/human TGFβ1 Rec BAC TG mice, TGFβ1 concentrations in the blood are useful in the development confirmation of pulmonary fibrosis.

Depending on the organ to cause fibrosis, the effect on TGFβ1 in the blood may be different. Therefore, by specifically expressing human TGFβ1 in each organ, detailed analysis becomes possible and the usefulness of TGFβ1 as a marker can be studied.

In FIG. 15, 3000 pg/ml of human TGFβ1 concentration in plasma was the cut-off value. It is also possible to determine the cut-off value for each age group by accumulating data on the number of measured mice and age. By identifying the timing and possibility of onset at a younger stage, it is possible to stabilize the provision of research TG mice.

According to FIG. 15B, by using 300 pg/ml of human TGFβ1 concentration in the urine as a cut-off value, mice having more than the cut-off value of TGFβ1 concentration in the urine can be determined that they have pulmonary fibrosis even without CT findings. It is within the scope of the present invention that it is possible to increase the accuracy of judgment of renal fibrosis and severity of renal fibrosis by measuring TGFβ1 concentrations in both plasma and urinary.

In FIG. 15B, some data showed higher concentrations of TGFβ1 and other data showed lower concentrations in each mouse. In the group with high TGFβ1 concentrations, it is considered that TGFβ1 is the main cause of fibrosis. In the group with low TGFβ1 concentrations, as the TGFβ1 concentrations of mouse Podocin/TGFβ1 TG mice were higher than those of healthy subjects, it could be used as one of the significant markers for estimating the symptoms. As shown in mice data, by further accumulating data in the future, according to plasma TGFβ1 concentrations in human pulmonary fibrosis, measurements of human plasma TGFβ1 concentrations and cut-off value may detect human pulmonary fibrosis with high accuracy.

As shown in FIGS. 16 and 17, it can bee seen that determination of lung fibrosis in TG mice is easy by using plasma TGFβ1 concentrations of TG mice and predetermined cut-off value. For making TG mice with lung fibrosis, another gene different from that of TG mice with kidney fibrosis is introduced, furthermore, breeding is carried out with a load such as smoke inhalation of tobacco. By combining the preparation method and the growth method, the determination of lung fibrosis and renal fibrosis can be easily performed. As described above, if both urinary TGFβ1 concentrations and plasma TGFβ1 concentrations are combined and judged, it is also possible to determine whether the site of fibrosis occurrence is lung or kidney. Since all of fibrosis in human occur spontaneously, a judgment index based on a combination with a gene integration method like TG mice can not be thought. Therefore, as described above, by measuring the concentrations of TGFβ1 in several types of bodily fluids other than blood and urine, after the cut-off value by accumulating data of TGFβ1 concentrations for each bodily fluid in the future is determined, it will be easy to estimate which internal organ develops fibrosis. The application is included in the technical scope of the present invention.

In mice, when determining the cut-off value of TGFβ1 concentrations, from the same train group, and can either be determined a cut-off value by accumulating data, separate or development groups were determined statistically from the past stored data, it is also possible to use a cut-off value. When determining the cut-off value of TGFβ1 concentrations in mice, it is possible to set up the cut-off value by accumulating data from the same breeding group, or by statistically determined from another breeding group or past accumulated data.

<Kit for Assessing the Condition of Transgenic Mice>

Next, we will explain the contents of a kit for assessing the condition of transgenic mice expressing human TGFβ1.

The kit contains at least (1) an instrument for collecting a bodily fluid from a transgenic mouse, (2) a tube to separate a component including human TGFβ1 from the collected bodily fluid, and (3) a measuring thing for human TGFβ1.

(1) When collecting blood as a bodily fluid, as the instrument, a small glass tube for collecting blood from the fundus, or a razor and a small glass tube for collecting blood from the tail vein, or a syringe for collecting blood from tarsal, carotid artery, jugular vein, heart, abdominal aorta, abdominal aorta and the like is used. When using the blood, it is preferable to attach an anticoagulant (heparin, EDTA, and citric acid) in order to separate the plasma. In the case of using a micro glass tube, it is preferable to use heparin on the inner wall surface. Also, it is possible, if necessary, chemicals for anesthesia (pentobarbital, thiopental, ketamine, ether, isoflurane, sevoflurane, etc.) can be combined.

Also, in the case of collecting urine as bodily fluid, a watch glass or a metabolic cage is used.

(2) In the case of using blood as bodily fluid, a tube (a centrifuge tube) having a capacity of about 30 μL to 1 mL can be used.

(3) For ELISA, a plate with an appropriate number of wells (for example, 96-wells, 192-wells or 384 wells), the first antibody solution (not recognizing the mouse TGFβ1) that specifically recognizes the human TGFβ1, the second antibody solution specifically recognizing the human TGFβ1 which is used for the sandwich method, an antibody for color development which recognizes the second antibody, and a reagent for color development can be provided.

A procedure for measuring human TGFβ1 concentrations in the blood of transgenic mice using the kit will be briefly described.

First, after placing the transgenic mouse into a preservative, gently warm the tail to dilate the blood vessel (at this time, the animal itself can be expanded by keeping it for several minutes). Scald the tail with a scalpel so that the incision is opened and blood is allowed to drip and is collected using a micro glass tube (hematocrit tube). This method can be carried without killing the mouse, it is preferable to see the changes over time. It is also possible to be bled from the outer tarsal vein. Further, if the mouse may be killed, it is possible to collect a large amount of blood (about several hundred μL to 1 mL) from heart, abdominal aorta, abdominal vena cava using a syringe with a needle under anesthesia.

The collected blood is transferred to a tube and centrifuged at 1000 to 1500×g for 15 to 30 minutes at 4° C. to separate and collect plasma component containing human TGFβ1. When diluting the plasma component in order to improve the measurement accuracy, the dilution ratio is reflected in the measurement result.

The concentration of TGFβ1 in plasma is measured by an ELISA system. When a sandwich method is used, the first antibody is coated on the solid phase of the ELISA plate, the solid phase is blocked with BSA or the like, and the sample plasma (or diluted appropriately) is added. After binding the first antibody with human TGFβ1, the solution in the well is removed and the well is washed several times with PBS. Then, a second antibody is added to the well, after binding the second antibody with the first antibody bound to human TGFβ1, the solution in the well is removed and the well is washed several times with PBS. Next, a labeled antibody that recognizes the second antibody is added to the well and reacted, and then the solution in the well is removed. After that, the well is washed several times with PBS, and color development reagent is added to the well. After an appropriate time, the degree of color development is measured using a plate reader. The human TGFβ1 concentrations in samples are determined based on the calibration curve which are measured at the same time.

By comparing the concentration of human TGFβ1 in the blood of the transgenic mouse in this way with the cut-off value, the pathogenesis of the transgenic mouse can be evaluated.

<Kit for Diagnosing Fibrosis in Human>

Next, we will explain the contents of a kit for diagnosing fibrosis in human.

The kit contains at least (1) an instrument for collecting a bodily fluid from a subject, (2) a tube to separate a component including human TGFβ1 from the collected bodily fluid, and (3) an ELISA system for measuring human TGFβ1.

(1) When collecting blood as a bodily fluid, a syringe with a needle is preferably used as the instrument. When using the blood, it is preferable to attach an anticoagulant (heparin, EDTA, and citric acid) in order to separate the plasma. When collecting urine as bodily fluid, a catheter is used.

(2) In the case of using blood as bodily fluid, a tube (a centrifuge tube) having a capacity of about 1 ml to 30 mL can be used.

(3) For ELISA, a plate with an appropriate number of wells (for example, 96-wells, 192-wells or 384 wells), the first antibody solution that specifically recognizes the human TGFβ1, the second antibody solution specifically recognizing the human TGFβ1 which is used for the sandwich method, an antibody for color development which recognizes the second antibody, and a reagent for color development can be provided.

A procedure for measuring human TGFβ1 concentrations in the blood of transgenic mice using the kit will be briefly described.

First, blood is collected using a syringe with a needle. The collected blood is transferred to a tube and centrifuged at 1000 to 1500×g for 15 to 30 minutes at 4° C. to separate and collect plasma component containing human TGFβ1.

The method of determining the TGFβ1 concentrations in plasma by the ELISA system follows the method described in above <Kit for assessing the condition of transgenic mice>.

By comparing the concentration of human TGFβ1 in the blood in this way with the cut-off value, a data for assessing the degree progression of human fibrosis can be obtained. Finally, an expert such as a medical doctor will judge it.

As mentioned above, based on the present embodiments, a TG mouse specifically expressing human TGFβ1 in the kidney and developing spontaneous renal fibrosis was provides. The transgenic mouse naturally develops renal fibrosis and renal failure at 15 weeks of age, and begins to die at 20 to 26 weeks of age. By using the TG mouse that develops the disease in early life stage and lives relatively long, research on kidney related diseases (including glomerulosclerosis, renal failure, diabetic nephropathy, hypertension-related renal disorders, kidney cancer, peritoneal fibrosis, etc.) can be dramatically developed.

The invention claimed is:

1. A transgenic mouse having a genome comprising:
   a mouse Podocin promoter, and
   the entire gene region of human transforming growth factor beta-1 (human TGFβ1) located downstream of the mouse Podocin promoter,
   wherein expression of the human TGFβ1 is controlled by the mouse Podocin promoter,
   the human TGFβ1 contains 7 exons and 6 introns,
   the human TGFβ1 is expressed in a kidney of the mouse as non-active TGFβ1 and becomes active TGFβ1 extracellularly, and
   the transgenic mouse spontaneously develops renal fibrosis.

2. The transgenic mouse according to claim 1, wherein the transgenic mouse starts to develop renal fibrosis spontaneously from the age of 15 weeks.

3. The transgenic mouse according to claim 2, wherein the transgenic mouse is derived from the mouse line C57BL/6J.

4. A method for producing the transgenic mouse according to claim 1, comprising:
   1) incorporating a positive/negative selection marker cassette into intron 1 of a human TGFβ1 gene in a Bacterial Artificial Chromosome (BAC) construct;
   2) incorporating homology arms of 54-58 bases in length that target a mouse Podocin promoter into the BAC such they flank the human TGFβ1 gene obtained in step 1);
   3) inserting the human TGFβ1 gene flanked by homology arms obtained in step 2) into a mouse Podocin gene in a BAC construct such that the human TCGβ1 gene and the positive/negative selection marker cassette are operably linked to a mouse Podocin promoter;
   4) removing a nucleic acid sequence encoding the human TGFβ1 and the positive/negative selection marker cassette operably linked to the mouse Podocin promoter from the BAC construct obtained in step 3);
   5) purifying and microinjecting the nucleic acid sequence obtained in step 4) into a mouse embryo such that the transgenic mouse of claim 1 is obtained.

5. A method for evaluating the presence of pulmonary fibrosis in the transgenic mouse of claim 1, comprising:
   measuring the concentration of human TGFβ1 in the plasma or urine of the transgenic mouse of claim 1, wherein a concentration of human TGFβ1 of at least 3000 pg/ml in the plasma or at least 300 pg/ml in urine indicates the mouse has pulmonary fibrosis.

6. A method of inducing diabetes in the transgenic mouse of claim 1, comprising:
   1) waiting for the transgenic mouse of claim 1 to spontaneously develop renal dysfunction and renal fibrosis; and
   2) administering streptozotocin (STZ) to the mouse obtained in step 1) such that diabetes is induced.

7. The method of inducing diabetes in the transgenic mouse of claim 1, comprising:
   1) waiting for the transgenic mouse of claim 1 to spontaneously develop renal dysfunction and renal fibrosis after 15 weeks of age; and
   2) administering streptozotocin (STZ) to the mouse obtained in step 1) after 16 weeks of age such that diabetes is induced.

* * * * *

SEQUENCE LISTING

```
<160> NUMBER OF SEQ ID NOS: 12

<210> SEQ ID NO 1
<211> LENGTH: 35
<212> TYPE: DNA
<213> ORGANISM: Artificial
<220> FEATURE:
<223> OTHER INFORMATION: TGFbeta1-H1

<400> SEQUENCE: 1
atgccgccct ccgggctgcg gctgctgccg ctgct                           35

<210> SEQ ID NO 2
<211> LENGTH: 34
<212> TYPE: DNA
<213> ORGANISM: Artificial
<220> FEATURE:
<223> OTHER INFORMATION: TGFbeta1-H2

<400> SEQUENCE: 2
caacatgatc gtgcgctcct gcaagtgcag ctga                            34

<210> SEQ ID NO 3
<211> LENGTH: 30
<212> TYPE: DNA
<213> ORGANISM: Artificial
<220> FEATURE:
<223> OTHER INFORMATION: TGFbeta1-H3

<400> SEQUENCE: 3
aggcgctgga gaaagttgac ccagagcttg                                 30

<210> SEQ ID NO 4
<211> LENGTH: 30
<212> TYPE: DNA
<213> ORGANISM: Artificial
<220> FEATURE:
<223> OTHER INFORMATION: TGFbeta1-H4

<400> SEQUENCE: 4
ccttcttgaa tctttccacc tcaggacccc                                 30

<210> SEQ ID NO 5
<211> LENGTH: 56
<212> TYPE: DNA
<213> ORGANISM: Artificial
```

```
<220> FEATURE:
<223> OTHER INFORMATION: Podocin-H5

<400> SEQUENCE: 5
gctggggctg cgactctgcc agcagctggc tccggggttg caccgctgca ttgaga      56

<210> SEQ ID NO 6
<211> LENGTH: 56
<212> TYPE: DNA
<213> ORGANISM: Artificial
<220> FEATURE:
<223> OTHER INFORMATION: Podocin-H6

<400> SEQUENCE: 6
gcgaatgggc aaaggctgtg tgaatctgcc atataaagcc acatccctga gagagg      56

<210> SEQ ID NO 7
<211> LENGTH: 22
<212> TYPE: DNA
<213> ORGANISM: Artificial
<220> FEATURE:
<223> OTHER INFORMATION: hTGFbeta1-forward

<400> SEQUENCE: 7
aagactatcg acatggagct gg                                           22

<210> SEQ ID NO 8
<211> LENGTH: 22
<212> TYPE: DNA
<213> ORGANISM: Artificial
<220> FEATURE:
<223> OTHER INFORMATION: hTGFbeta1 reverse

<400> SEQUENCE: 8
gtatcgccag gaattgttgc tg                                           22

<210> SEQ ID NO 9
<211> LENGTH: 24
<212> TYPE: DNA
<213> ORGANISM: Artificial
<220> FEATURE:
<223> OTHER INFORMATION: hGAPDH forward

<400> SEQUENCE: 9
ccacccatgg caaattccat ggca                                         24

<210> SEQ ID NO 10
<211> LENGTH: 24
<212> TYPE: DNA
<213> ORGANISM: Artificial
<220> FEATURE:
<223> OTHER INFORMATION: hGAPDH reverse

<400> SEQUENCE: 10
tctagacggc aggtcaggtc cacc                                         24

<210> SEQ ID NO 11
<211> LENGTH: 25
<212> TYPE: DNA
<213> ORGANISM: Artificial
<220> FEATURE:
<223> OTHER INFORMATION: mGAPDG forward

<400> SEQUENCE: 11
cccttattga cctcaactac atggt                                        25
```

```
<210> SEQ ID NO 12
<211> LENGTH: 23
<212> TYPE: DNA
<213> ORGANISM: Artificial
<220> FEATURE:
<223> OTHER INFORMATION: mGAPDH reverse

<400> SEQUENCE: 12
gaggggccat ccacagtctt ctg                                              23
```